US007572890B2

(12) United States Patent
Wakamiya

(10) Patent No.: US 7,572,890 B2
(45) Date of Patent: Aug. 11, 2009

(54) RECOMBINANT HUMAN MANNAN-BUILDING PROTEINS

(75) Inventor: Nobutaka Wakamiya, Ibaraki (JP)

(73) Assignee: Fuso Pharmaceutical Industries, Ltd., Osaka (JP)

(*) Notice: Subject to any disclaimer, the term of this patent is extended or adjusted under 35 U.S.C. 154(b) by 366 days.

(21) Appl. No.: 11/241,035

(22) Filed: Sep. 30, 2005

(65) Prior Publication Data

US 2006/0040362 A1 Feb. 23, 2006

Related U.S. Application Data

(62) Division of application No. 10/054,536, filed on Jan. 22, 2002, now Pat. No. 7,049,099, which is a division of application No. 09/600,950, filed as application No. PCT/JP98/03311 on Jul. 23, 1998, now abandoned.

(30) Foreign Application Priority Data

Jan. 23, 1998 (JP) .................................. 10-11864

(51) Int. Cl.
*C07K 14/00* (2006.01)
*A61K 38/16* (2006.01)

(52) U.S. Cl. ........................ 530/350; 530/380; 530/827

(58) Field of Classification Search ................. 530/350, 530/827, 380
See application file for complete search history.

(56) References Cited

U.S. PATENT DOCUMENTS

| | | | | |
|---|---|---|---|---|
| 5,270,199 | A | 12/1993 | Ezekowitz | 435/240.2 |
| 2004/0170653 | A1* | 9/2004 | Stanislawski et al. | 424/277.1 |

FOREIGN PATENT DOCUMENTS

| | | |
|---|---|---|
| JP | 2504581 | 12/1990 |
| WO | WO-8901519 | 2/1989 |
| WO | WO-9855614 | 12/1998 |

OTHER PUBLICATIONS

Katushiro Ooya et al. (Nippon Men'eki Gakkai Soaki, Gakujutsu Shukai Kiroku 27: 182, Sep. 29, 1997—Original and English translation.*

Eda, et al., "Characterization of Truncated Human Mannan-Binding Protein (MBP) Expressed in *Escherichia coli*," Biosci. Biotechnol. Biochem., 62(7): 1326-1331 (1998).

Epstein, et al., "The collections in innate immunity," Current Opinion in Immunology, 8:29-35 (1996).

Ezekowitz, R.A.B. et al., "Mannose-binding protein and susceptibility to chronic hepatitis B infection," The Lancet, 348:1396-1397 (Nov. 1996).

Ezekowitz, R.A.B. et al.; "A Human Mannose-binding Protein is an acute-phase Reactant that Shares Sequence Homology with Other Vertebrate Lectins," J. Exp. Med., 167:1034-1046 (Mar. 1988).

Fujita, T., "Complement activation and Lectin Pathway," Rinsho-Meneki, 29(3):405-410 (1997). (Japanese with English abstract translation).

Garred, et al. , Susceptibility to HIV infection and progression of AIDS in relation to variant alleles of mannose-binding lectin,: The Lancet, 349:236-240 (Jan. 1997).

Kawai, et al., "Cloning and characterization of a cDNA encoding bovine mannan-binding protein," Gene, 186(2);161-165 (Feb. 1997).

Kurata, H., "Structure and Function of Mannan-Binding Proteins Isolated from Human Liver and Serum," J. Biochem., 115(6);1148-1154 (1994).

Lim, et al., "Primary Structure of Bovine Collection-43 (CL-43) Comparison with conglutinin and lung surfactant protein-D," J. Biol. Chem., 269(16):11820-11824 (Apr. 1994).

Lipscombe, et al., "Mutations in the Human Mannose-Binding Gene: Frequencies in several population groups," European Journal of Human Genetics, 4(1);13-19 (1996).

Lu, et al., "Purification, characterization and cDNA cloning of human lung surfactant protein D," Biochem. J., 284:795-802 (1992).

Ma, et al., "Functional Expression of Human Mannan-Binding Proteins (MBPs) in Human Hepatoma Cell Lines Infected by Recombinant Vaccinia Virus: Post-Translational Modification, Molecular Assembly, and Differentiation of Serum and Liver MBP," J. Biochem. 122:810-818 (1997).

Malhortra, et al., "Glycosylation changes of IgG associated with rheumatoid arthritis can activate complement via the mannose-binding protein," Nature Medicine, 1(3); 237-243 (Mar. 1995).

Malhortra, et al., "Interaction of C1q receptor with lung surfactant protein A", Eur. J. Immun., 22:1437-1445 (1992).

Matsuda, et al., "Involvement of Mannan Binding Protein with crisis and progression of IgA nephrosis," Journal of Nephrology Association of Japan, 39(3):235 (1997). (Japanese with English abstract translation).

Nepomuceno, et al., "cDNA Cloning and Primary Structure Analysis of ClqR(p), the Human CI1/MBL/SPA Receptor That Mediates Enhanced Phagocytosis in Vitro," Immunity, 6(2):119-129 (Feb. 1997).

Sastry, et al., "The Human Mannose-binding Protein Gene: Exon Structure Reveals its Evolutionary Relationship to a Human Pulmonary Surfactant Gene and Localization to Chromosome 10," J. Exp. Med., 170:1175-1189 (Oct. 1989).

Sumiya, et al., "Mannose-binding protein, genetic variant and the risk of infection," Q. J. Med., 89:723-726 (1996).

Sumiya, et al., "Molecular basis of opsonic defect in immunodeficient children," Lancet, 337:1569-1570 (Jun. 1991).

Super, et al., "Association of Low Levels of Mannan-binding Protein with a Common Defect of Opsonisation," Lancet, 2: 1236-1239 (Nov. 1989).

Suzuki et al., "Characterization of Recombinant Bovine Conglutinin Expressed in a Mammalian Cell," Biochem Biophys Res Commun, 238, 856-863 (1997).

*Primary Examiner*—S. Devi
(74) *Attorney, Agent, or Firm*—Marshall, Gerstein & Borun LLP

(57) ABSTRACT

Recombinant Human Mannan-Binding Proteins (rhMBP) having physiological activities which are substantially identical to those offered by Human Mannan-Binding Proteins (hMBP), as well as, in particular, a production system for homogenously producing rhMBP having the specific peaks at the molecular weight of 1,000~1,300 kDa determined by absorbance (280 nm) in Gel-Filtration Chromatography are provided.

4 Claims, 22 Drawing Sheets

OTHER PUBLICATIONS

Suzuki et al., :Cloning and Sequencing of a cDNA Coding for Bovine Conglutinin, Biochem Biophys Res Commun, 191/2, 335-342 (1993).

Tan et al., "Improvements on the purification of mannan-binding lectin and demonstration of its CA2+-independent association with a C1s-like serine protease," Biochem. J. 391, 329-332 (1996).

Taylor, et al., "Structure and evolutionary origin of the gene encoding a human serum mannose-binding protein," Biochem J., 262: 763-771 (1989).

Thomas, et al., "Mutation of gene for mannose-binding protein associated with chronic hepatitis B viral infection," Lancet, 348: 14176-1419 (Nov. 1996).

Uemura, et al., "Correlation Between Structure and Function of Calcium Dependence Animal Lectin on Host Defense," Jikken-Igaku, 13(18) (1995). (Japanese with English abstract translation).

Wakamiya, et al., "Anti-Viral Activity by Collectin," Rinsho Meneki, 29(4); 508-513 (1997). (Japanese with English abstract translation).

Wakamiya, et al., "Isolation and Characterization of Conglutinin as an Influenza A Virus Inhibitor," Biochem. Biophys. Res. Comm., 187: 1270-1278 (Sep. 1992).

Wakamiya, et al.,"The Mannose Binding Protein and Conglutinin in Bovine Serum Have an Antiviral Activity Against Influenza Virus," Glycoconjugate Journal, 8:235 (1991).

* cited by examiner

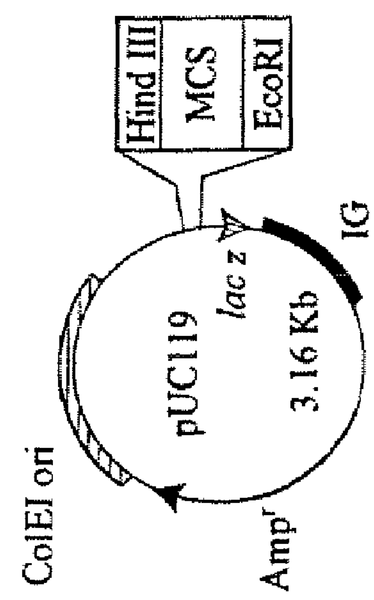
EcoR I + Hind III digestion
CV3 linker ligation
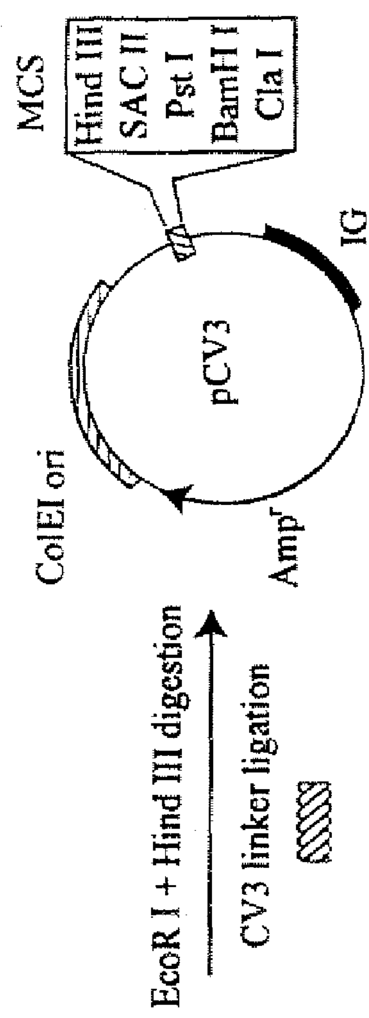
FIG. 3

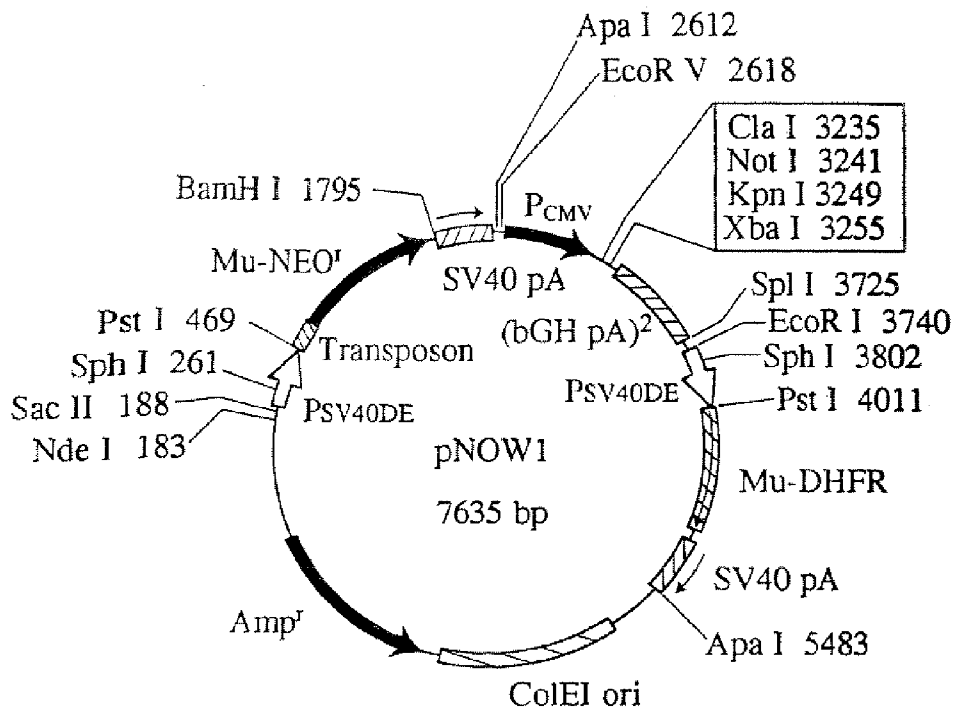

| | |
|---|---|
| Amp$^r$ | Ampicillin Resistance Gene |
| (bGHpA)$^2$ | Bovine Growth Hormone Polyadenylation Signal |
| ColEI | Escherichia coli Replication Origin |
| Mu-DHFR | DHFG Gene introduced thereinto Mutation |
| MU-NEO$^r$ | Neomycin Resistance Gene introduced thereinto Mutation |
| Pcmv | Human Cytomegalovirus Major Immediate-Early Antigen Promoter |
| PSV40DE | Attenuated SV40 Promoter (including SV40 Replication Origin) |
| SV40pA | SV40 Polyadenylation Signal |
| Transposon | Transposon Sequence |

FIG. 11

1. native hMBP
2. rhMBP ( with Vitamin C )
3. rhMBP ( without Vitamin C )

RECOMBINANT HUMAN MANNAN-BUILDING PROTEINS

This application is a divisional application of U.S. patent application Ser. No. 10/054,536, filed, Jan. 22, 2002, now U.S. Pat. No. 7,049,099, which is a divisional application of U.S. patent application Ser. No. 09/600,950 filed Sep. 9, 2000, now abandoned, which is a 35 USC § 371 national stage application of International patent application No. PCT/JP98/03311, filed on Jul. 23, 1998, which claims priority to Japanese application Hei 10-11864, filed on Jan. 23, 1998.

TECHNICAL FIELD

The present invention relates to the novel recombinant human Mannan-Binding Proteins (hereinafter simply referred to as "rhMBP") having anti-microorganism activities, in particular, anti-influenza-virus activities and producing method of the same.

BACKGROUND ART

Mannan-Binding Proteins (hereinafter simply referred to as "MBP" and sometimes called as Mannose-Binding Proteins, Mannose-Binding Lectin (MBL) or Mannan-Binding Lectin (MBL)). Conglutinin, Surfactant Protein A (SP-A) and Surfactant Protein D (SP-D), and each of them belongs to a group called as collectin.

With reference to FIG. 1, collectin comprises basic constituent unit having the four unique regions of (1) calcium ion ($Ca^{2+}$)-dependent carbohydrate recognition domain (CRD), (2) neck region, (3) collagen-like region and (4) N-terminal region containing cystein [Malhotra et al., *European Journal of Immunology*, Vol. 22, pp. 1437-1445 (1992)], then triple helix are formed by twisting three constituent units (three units) at each of their collagen-like region, and subunits are formed.

Such subunits may further constitute oligomer structure like trimer, tetramer or hexamer. Of the collectins, MBP is specifically binding to Mannose or N-Acetyl-Glucosamine and needs calcium (ion) for such binding, for example, form of MBP from the human serum is homopolymer having, as the constituent units, the subunits in the molecular weight of about 32,000 Da [Teizo Fujita, "Complement Activation and Lectin Pathway", *Rinsho-Meneki*, Vol. 29, No. 3, pp. 405-410 (1997)].

In vertebrates, mechanisms involving specific antibody reaction and immune response through the cells are considered as a main host-defense system against inversion of the pathogenic bacteria. However, recently, non-specific immune response by these lectins seems that it may play an important role to neutralize and remove the various microorganisms and virus in the puerile subjects having the maternal transmigration antibody and the undeveloped specific defense system [Super et al., *Lancet*, Vol. II, pp. 1236-1239 (1989): Nobutaka Wakamiya, Yasuhiko Suzuki, "Anti-Viral activity by Collectin" *Rinsho-Meneki*, Vol. 29, No. 4, pp. 508-513 (1997)].

Then, regarding the role of these lectins on biological defense in host organism, it is reported that infection will be easily spread by, for example, the reduction of MBP concentration in blood due to the genetic mutation of MBP gene [Sumiya et al. *Lancet*, Vol. 337, pp. 1569-1570 (1991)].

The present inventor once reported that the conglutinin and MBP inhibit infection and hemaggulutination inhibition activities of H1 and H3 Type Influenza A Viruses [Wakamiya et al. *Glycoconjugate Journal*, Vol. 8, p. 235 (1991); Wakamiya et al., *Biochem. Biophys. Res. Comm*., Vol. 187, pp. 1270-1278 (1992)].

In particular, with respect to the human MBP (hereinafter simply referred to as "hMBP"), many aspects including their structure and their physiological functions (activities) have recently been investigated eagerly. For example, Ezekowitz et al., reported the analysis results on the hMBP structure as their structure and their gene [Epstein et al. "The collectins in innate immunity", *Current Opinion in Immunology*, Vol. 8, pp. 29-35, (1996); Japanese Patent Translation Publication No. 2-504581]

On the other hand, as an aspect on biological-function of hMBP, hMBP have been considered that it involves with basal immunity like (i) anti-microbial activities, (ii) opsonin activities, (iii) complement activation [Kazuhide Uemura, et al., "Correlation between Structure and Function of Calcium Dependence Animal Lectin on Host Defence", Jikken-Igaku, Vol. 13, No. 18 (1995)]. With respect to an clinical application, in view of the findings obtained through analysis on deficit of MBP in blood, it had also been reported that cause of such deficit is gene mutation in collagen-like structure and, thereby, amino acids mutation, and, accordingly, both stabilities of MBP itself and MBP concentration in blood were reduced [Sumiya et al., "Mannose-binding protein, genetic variants and the risk of infection", *Q. J. Med*., No. 89. pp. 723-726 (1996); Thomas et al., "Mutation of gene for mannose-binding protein associated with chronic hepatitis B viral infection", *The Lancet*, Vol. 348, pp. 1417-1419 (1996); Ezekowitz, "Mannose-binding protein and susceptibility to chronic hepatitis B infection", *The Lancet*, Vol. 348, pp. 1396-1397 (1996)].

Also, it had been reported that MBP concentration in blood is concerned with a pathogenicity of hepatitis B viral and HIV infection. In contrast thereto, it has also been suggested that MBP may involve with lectin pathway through MBP, due to abnormalities on sugar chain of immunoglobulin, in the disorder like chronical rheumatoid arthritis [Malbotra et al., "Glycosylation changes of IgG associated with rheumatoid arthritis can activate complement via the mannose-binding protein", *Nature Medicine*, Vol. 1, pp. 237-243 (1995)] or IgA nephrosis [Mitsuhiro Matsuda et al., "Involvement of Mannan Binding Protein with crisis and progression of IgA nephrosis", *Journal of Nephrology Association of Japan*, vol. 39, No. 3, p. 235 (1997)]

Further, according to the recent studies, it had also been reported that, besides the susceptibility to HIV by hMBP, it may involve with latency prior to crisis of AIDS (Acquired Immuno Deficiency Syndrome), hMBP may therefore contribute to prolong the life of AIDS patients [Garred, et al., "Susceptibility to HIV infection and progression of AIDS in relation to variant alleles of mannose-binding lectin", *The Lancet*, Vol. 349, pp. 236-240 (1997)].

Unfortunately, although utilities of hMBP as physiologically active medical materials (components) have been expected, since the source of which is depended on the animal serum like human or rabbit serum, continuous production thereof was quite difficult and the yield thereof was very small. Further, artificial large scale production system for hMBP by gene recombination techniques have not yet been established.

DISCLOSURE OF INVENTION

The present inventions have been established through the continuous research to realize large-scale production of the homogenous hMBP in view of the aforenoted problems in the prior art.

Namely, hMBP (rhMBP) to be obtained by the present invention includes the characteristic rhMBP of:

rhMBP which offers the specific peaks at the molecular weight of 1,000~1,300 kDa, preferably 1,150 kDa, when it is applied to 280 nm absorbance in Gel-Filtration Chromatography:

rhMBP which offers the specific peaks at the molecular weight of 200~400 kDa, preferably 300 kDa, when it is applied to 280 nm absorbance in Gel-Filtration Chromatography: and rhMBP which offers the specific peaks at the molecular weight of 1,000~1,300 kDa and 200~400 kDa when it is applied to 280 nm absorbance in Gel-Filtration Chromatography.

The present invention may also includes rhMBP prepared according to the method comprising the steps of:

(1) constructing the expression vector pNOW1-hMBP by inserting into plasmid pNOW1 cDNA corresponding to 66 bp~812 bp of cDNA from natural Human Mannan-Binding Proteins (hereinafter simply referred to as "native MBP");

(2) preparing transformants by introducing said expression vector pNOW1-hMBP into Chinese Hamster Ovary (CHO) cells which are lack of dihydrofolate reductase ($dhfr^-$):

(3) obtaining neomycin resistance cells by culturing said transformants in a culture medium containing neomycin:

(4) obtaining methotrexate (MTX) resistance cells by culturing the selected neomycin resistance cells in a culture medium containing MTX; and (5) collecting rhMBP from the selected MTX resistance cells.

Amino acids which constitute native hMBP had already been analyzed and been reported by Herman et al [Sastry et al., "The human mannose-binding protein gene. Exon structure reveals its evolutionary relationship to a human pulmonary surfactant gene and localization to chromosome 10", *J. Exp. Med.* 170(4), 1175-1189 (1989)], a base sequence from its cDNA is set out in SEQ. ID. NO: 1 and a part of amino acids corresponding to such base sequence is set out in SEQ. ID. NO: 28.

Then, the present inventor planned to establish the production system of rhMBP by excising the particular base sequences involving protein expression of rhMBP, namely, cDNA (SEQ. ID. NO:2) corresponding to 66 bp~812 bp of the base sequences which constitute native hMBP, and incorporating it into an expression system.

BRIEF DESCRIPTION OF DRAWINGS

FIG. 3 shows a preparation scheme of Plasmid pCV3.

FIG. 11 shows the structure of Plasmid pNOW1.

BEST MODE FOR CARRYING OUT INVENTION rhMBP of the present inventions will be explained in detail along with the following Examples, but, as a matter of course, scope of the present invention should not be limited based on the disclosure of the Examples.

Examples are consisting of; construction of plasmid pNOW1 (Example 1), construction of expression vector pNOW1-hMBP (Example 2), collection of the expression clone from neomycin (G418) resistance cells and MTX resistance cells (Example 3), structural analysis of rhMBP by PAGE analysis and Gel-Filtration Chromatography (Example 4), evaluation of glyco-binding activities on rhMBP and native hMBP (Example 5), evaluation of activities for hemagglutination inhibition (HI) (Example 6), evaluation of neutralization activities (Example 7), evaluation of activities for viral growth (infection spread) inhibition (Example 8), and evaluation of activities on rhMBP for activating complement (Example 9).

EXAMPLE 1

Preparation of Plasmid pNOW1

Figure 1:
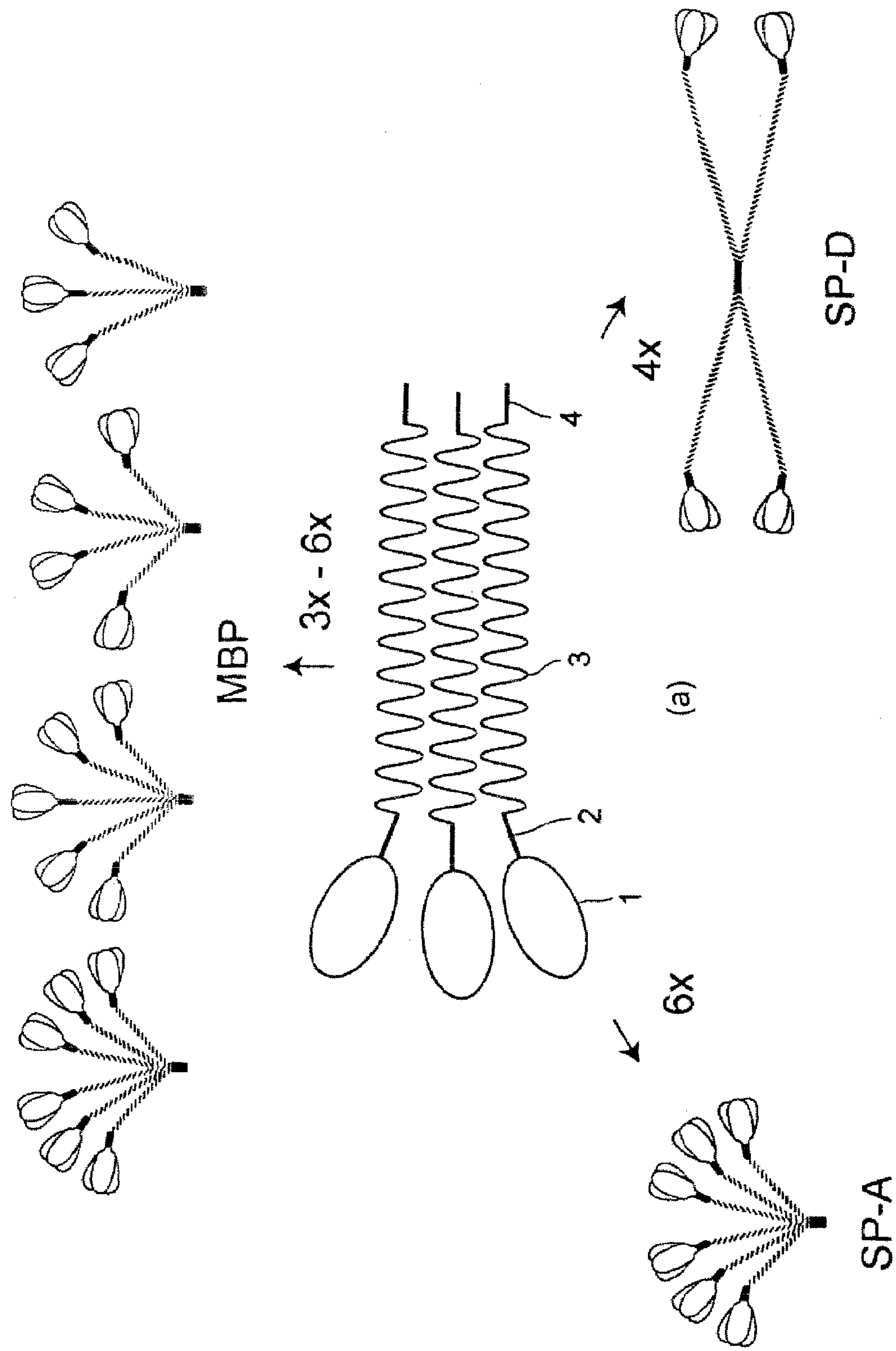
FIG. 1 shows a structure of collectins.
Figure 2:
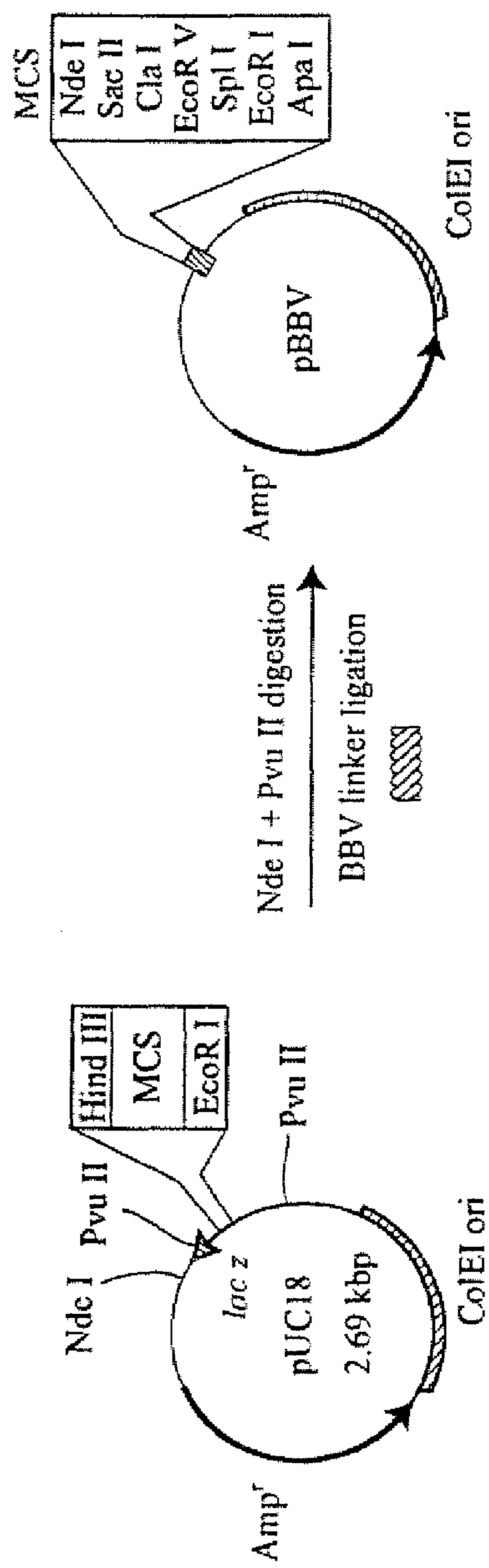
FIG. 2 shows a preparation scheme of Vector pBBV.

(1) Preparation of Back Bone Vector pBBV (FIG. 2)

Sense DNA having the base sequence set out in SEQ. ID. NO:3 and Anti-Sense DNA having the base sequence set out in SEQ. ID. NO:4 respectively were synthesized to additionally incorporate them as a linker (BBV linker) for multi-cloning sites into plasmid pUC18 (Takara Shuzo).

Sequence at site to be restricted by restriction enzymes in such linker is 3'-NdeI-SacII-ClaI-EcoRV-SplI-EcoRI-ApaI-5' and 5'-end thereof is Blunt End. Coding region for lacZ were completely removed by digesting 1 ng (0.1 μl) of plasmid pUC18 with restriction enzymes NdeI and PvuII.

Into this solution, 100 pmole of sense DNA and anti-sense DNA respectively for BBV linker were added, then 2.0 μl of solution I attached to DNA ligation kit Ver.2 (Takara Shuzo) were further added, and these were reacted at 16° C. for 30 minutes, 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of 50° C. medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto DNA of BBV linker were selected and designated them as vector pBBV.

(2) Preparation of Plasmid pCV3 (FIG. 3)

Multi-Cloning sites of plasmid pUC119 were removed. Then, sense DNA having the base sequence set out in SEQ. ID. NO:5 and Anti-Sense DNA having the base sequence set out in SEQ. ID. NO:6 respectively were synthesized to additionally incorporate them as a linker (CV3 linker) for multi-cloning sites into plasmid pUC119 (Takara Shuzo). Sequence at site to be restricted by restriction enzymes in such linker is 5'-HindIII-SacII-PstI-BamHI-ClaI-3' and 3'-end thereof is Blunt End. 1 mg (0.1 μl) of plasmid pUC119 was digested with the restriction enzymes HindIII and EcoRI.

Into the solution containing the plasmids so prepared, 100 pmole of sense DNA and anti-sense DNA respectively for CV3 linker were added, then 2.0 μl of solution I attached to DNA ligation kit Ver.2 (Takara Shuzo) were further added, and these were reacted at 16° C. for 30 minutes.

0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of 50° C. medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, Plasmids inserted thereinto DNA of CV3 linker were selected and designated them as plasmid pVC3 (for cloning the SV40-related gene).

Figure 4:
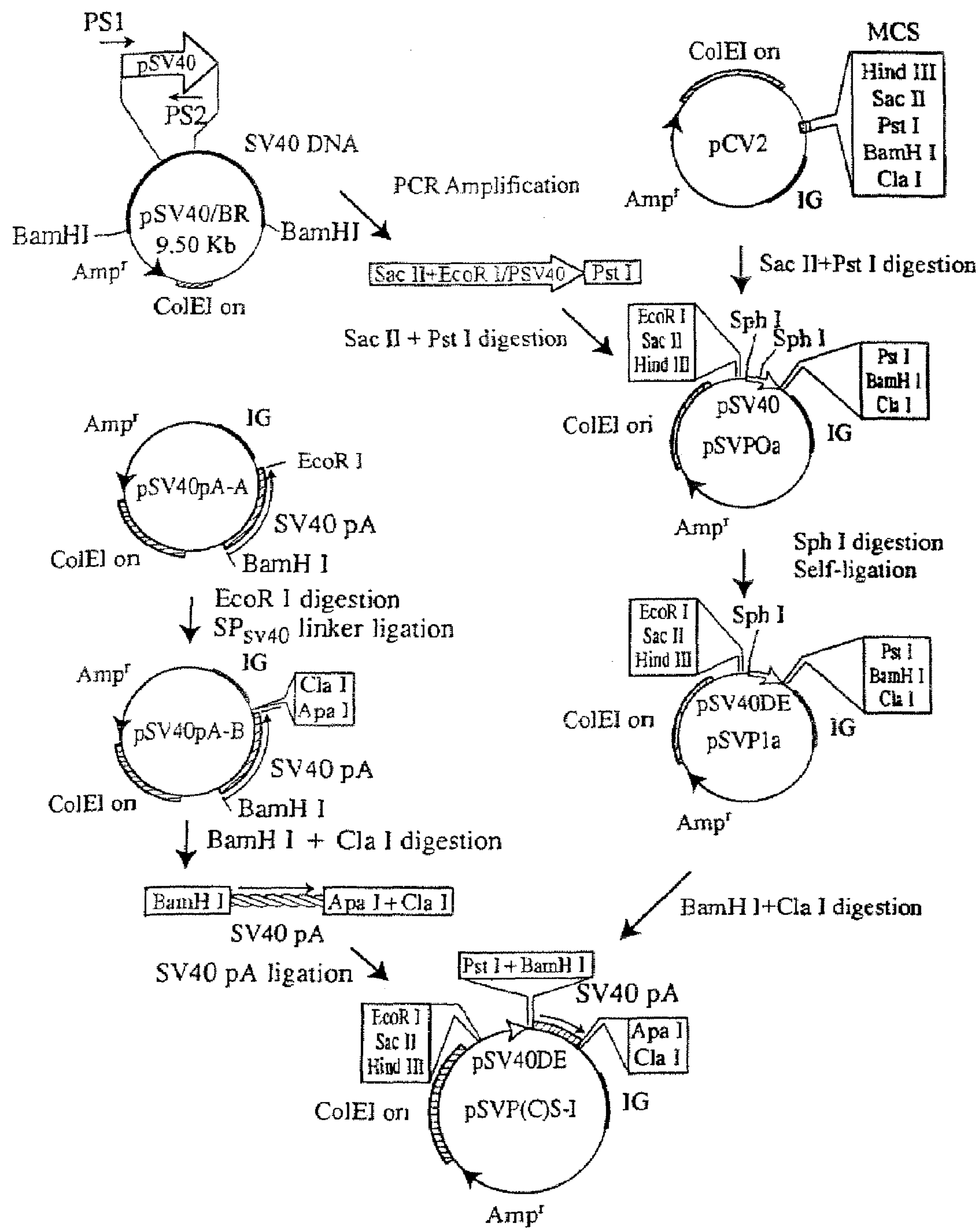
FIG. 4 shows a preparation scheme of Plasmid pSVP(D) S-1.

(3) Preparation of Plasmid pSVP(D)S-1 (FIG. 4)

(3-1) Preparation of Plasmid pSVP1a

5'-sense primer (PS1) having the base sequence set out in SEQ. ID. NO:7 and 3'-anti-sense primer (PS2) having the base sequence set out in SEQ. ID. NO:8 respectively were synthesized to excise SV40 initial promoter having SV40 Ori from plasmid pSV40/BR (obtained from Hiroshima University) containing the whole DNA of SV40 virus ligated with BamHI on pBR322. 5'-end of PS1 primer have restriction site of SacII-EcoRI instead of the PvuII site in the original sequence. Then, 3'-end of PS2 primer have PstI site instead of the original HindIII site. To 1 ng (0.1 μl) of pSV40/BR genome (from pSV40/BR, obtained from Hiroshima University), 100 pmole of PS1 primer and PS2 Primer respectively, 2.5 U (0.5 μl) of Taq polymerase (Takara Shuzo), 20 μl of PCR Buffer (250 mM Tris-HCl (pH 8.3 at 25° C.) 375 mM KCl, 15 mM $MgCl_2$). 1.0 μl of 100 mM DTT, 0.5 μl of 10 mM dNTP (10 mM dATP, dCTP, dGTP, dTTP) and 0.25 μl of acetylated BSA(4 mg/ml) were added, then were adjusted with the sterilized water to make its final volume 100 μl.

One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C.

Liquid phases were taken from this PCR reaction solution, and, to 10 μl of which, 2 μl of 10×H solution, 20 U (1 μl) of the restriction enzyme SacII as well as 20 U (1 μl) of the restriction enzyme PstI and 7 μl of the sterilized water were added and it was incubated at 37° C. for one hour. The reaction solution was then applied to an electrophoresis employing 0.8% agarose-gel at 50 mA for 30 minutes. Approximately 0.35 kb band was detected by exposuring it to the ultraviolet rays of 360 nm wavelength and was excised. These agarose fragments were poured into 1.5 ml tubes then the tubes were centrifuged at 15,000 rpm for 10 minutes, and DNA solution was obtained by separating the solution so produced with a pipet. Plasmid pCV3 were treated with SacII and PstI, then 5 μl of said DNA solution was added thereto, and 2.0 μl of solution I attached to DNA ligation kit Ver.2 (Takara Shuzo) were further added thereto, and these were incubated at 16' for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto DNA of SV40 promoter were selected and designated them as pSVOa. Plasmid pSVP1a containing $P_{SV_{40}DE}$ having SacII-EcoRI site at 5'-end thereof were further prepared by self-ligating such plasmids with the restriction enzyme SphI and removing its enhancer portion.

(3-2) Preparation of Plasmid pSVP1b

Plasmid pSVP1b containing SV40 Promoter $P_{SV40DE}$ for NEO gene cistron were prepared in accordance with the preparation scheme of Example 1 (3-1) except that 5'-sense primer (PS3) having the base sequence set out in SEQ. ID. NO:9 was synthesized instead of 5'-sense primer (PS1). P3 primer have SacII site only at 5'-end thereof (without EcoRI site).

(3-3) Preparation of SV40 polyA

Into 3'-end EcoRI site in SV40 polyA signal sequence of Plasmid pSV40pA-A (from pSV40/BR, obtained from Hiroshima University) having polyadenylation (herein referred to as "polyA") signal derived from SV40 virus genome, SPSV40 linker were ligated, thereby, EcoRI site was altered to ApaI-ClaI site. Firstly, as SPSV40 linker, sense DNA having the base sequence set out in SEQ. ID. NO:10 and anti-sense DNA having the base sequence set out in SEQ. ID. NO:11 respectively were synthesized.

1 ng (0.1 μl) of Plasmid pSV40pA-A was digested with the restriction enzyme EcoRI. Into the solution so prepared, 100 pmole of both sense DNA and anti-sense DNA for SPSV40 linker were added, then 2.0 μl of solution I attached to DNA ligation kit Ver.2 (Takara Shuzo) were further added thereto, and these were reacted at 16° for 30 minutes.

0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. After left it on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 μg/ml ampicillin respectively. After the overnight culture at 37° C. of the plasmids collected from the colonies so produced, plasmids inserted thereinto. DNA of SV40 polyA were selected and designated them as pSV40pA-B.

(3-4) Preparation of pSVP(D)S-1

To 1 ng (0.1 μl) of Plasmid pSV40pA-B, 20 U (1μl) of the restriction enzyme BamHI as well as 20 U (1 μl) of the restriction enzyme ClaI and 7 μl of the sterilized water were added, and it was reacted at 37° C. for one hour. The reaction solution was then applied to an electrophoresis employing 0.8% agarose-gel at 50 mA for 30 minutes. Approximately 0.8 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution using pipet. Plasmid pSV1a were treated with BamHI and ClaI, then 5 μl of said DNA solution was added thereto at the ratio of 1 ng per 0.1 μl of the solution, and 2.0 μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids additionally inserted thereinto DNA of SV40 polyA were selected and designated them as Plasmid pSVP(D)S-1.

Figure 5:
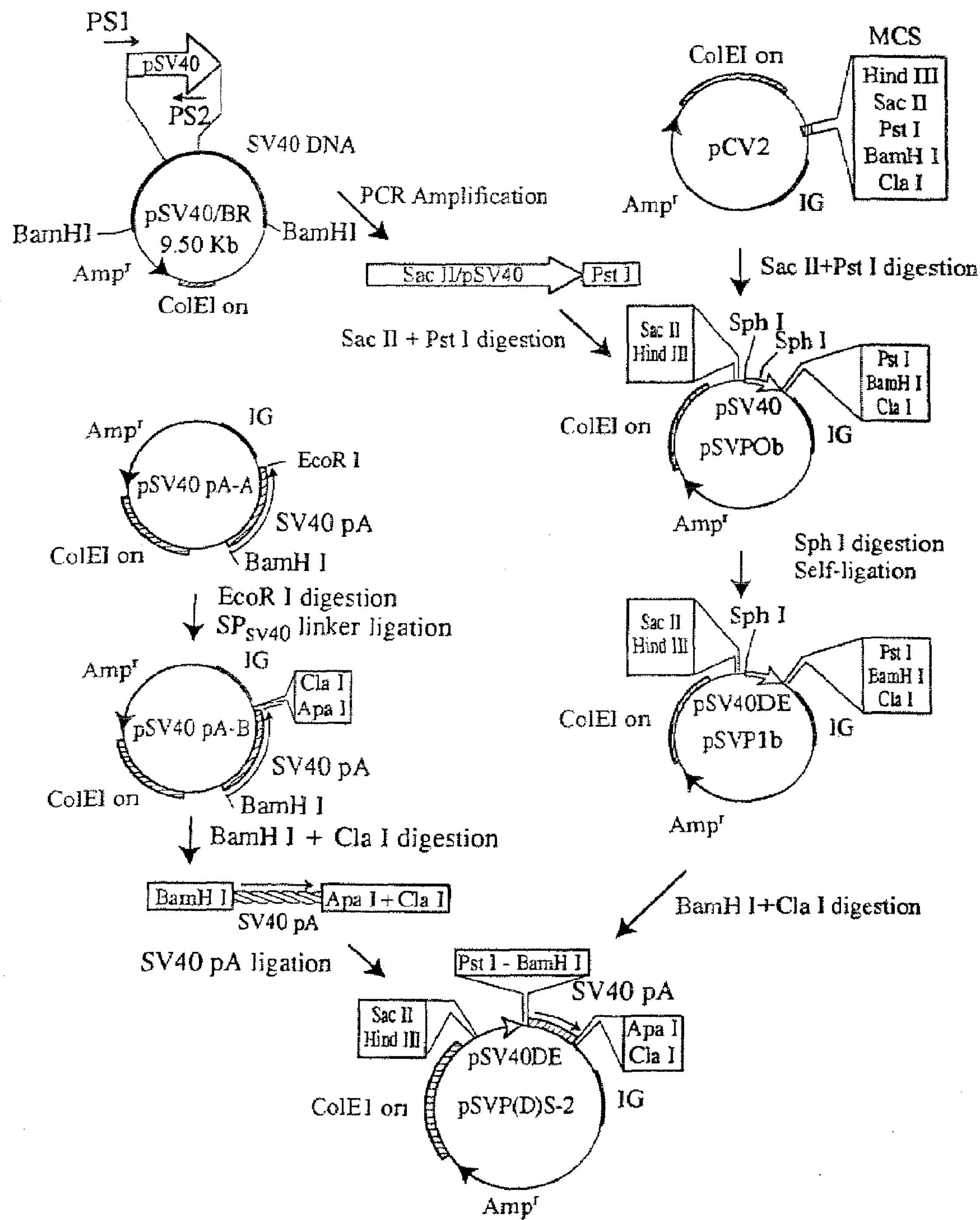
FIG. 5 shows a preparation scheme of Plasmid pSVP(D) S-2.

(4) Preparation of Plasmid pSVP(D)S-2 (FIG. 5)

Plasmid pSVP(D)S-2 containing SV40 Promoter for NEO gene cistron and SV40 polyA were prepared based on Plasmid pSVP1b and DNA of SV40 polyA from pSV40pA-B in accordance with the preparation scheme of Example 1 (3) for Plasmid pSVP(D)S-1.

Figure 6:
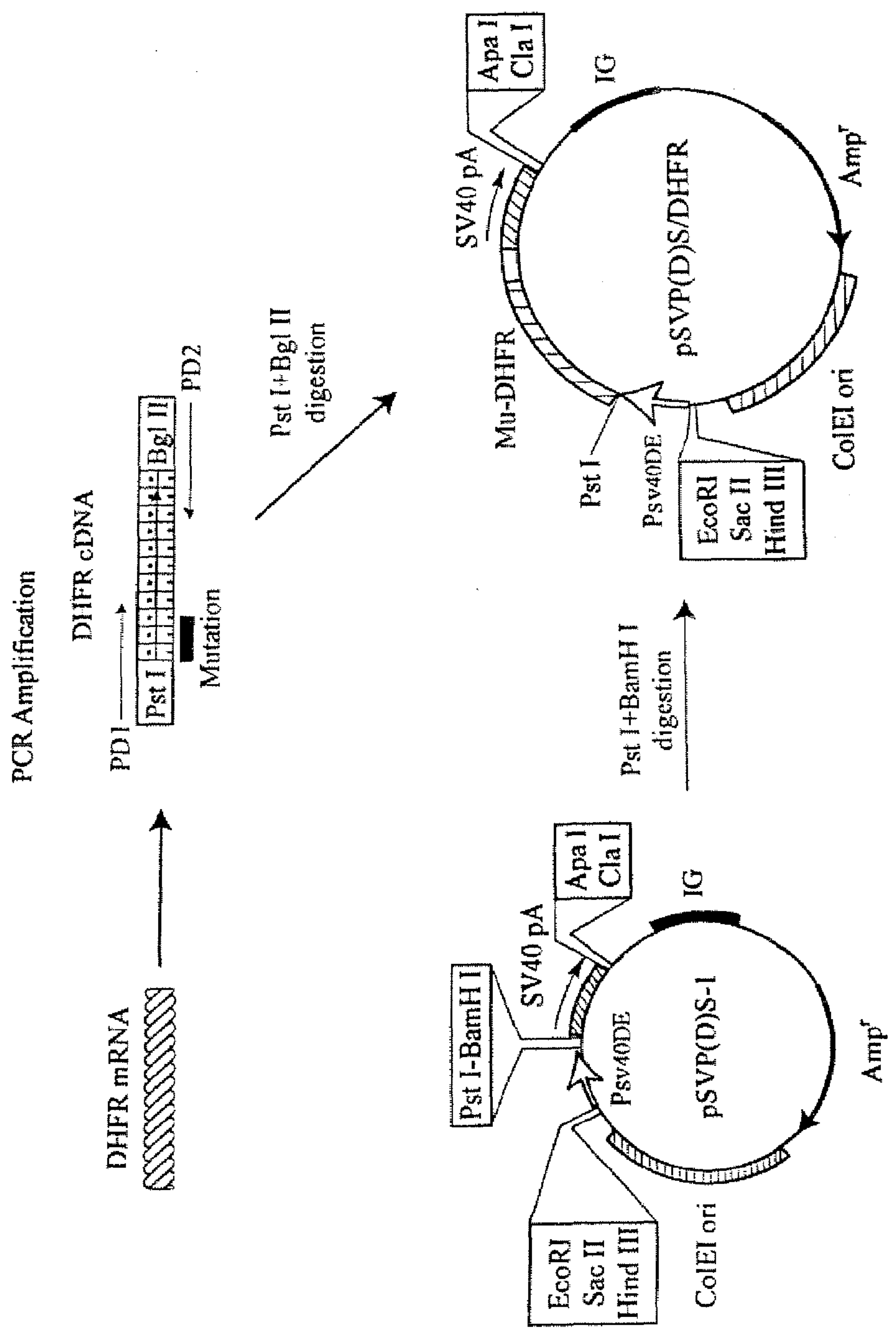
FIG. 6 shows a preparation scheme of Plasmid pSVP(D) S/DHFR.

(5) Preparation of Plasmid pSVP(D)S/DHFR (FIG. 6)

(5-1) Cloning on DHFR Gene mRNA were isolated from $10^7$ cells of cultured mouse fibroblast strain 3T3 according to guanidine isothiocyanate method (Meth. Enzymol., 152, p. 219, (1987)). Firstly, cells were floated in the flask, then the cells were re-floated in the sterilized PBS and transferred them to the centrifugation tubes. Under the temperature of 0° C. or below, the tubes were centrifuged at 450×g for 10 minutes, and the supernatant was then discarded. To the mix solution consisting of 6M GTG-CsCl, 10 mM sodium citrate, 0.1 ml β-mercaptoethanol and 0.5% sarcosil, cells so produced were added, then it was suspended and dissolved therein, and RNA were fragmented by passing it through 18-gauge needle. 2.5 ml of the solution so prepared was overlayered on 2.5 ml of the solution containing 5.7M CsCl, and 0.1M EDTA solution in an ultra-centrifugation tube. This was centrifuged at 35,000 rpm for 8 hours with an ultra-centrifugation, then the supernatant was discarded carefully, and RNA fractions deposited in the bottom of the tube were extracted with saturated phenol and were dissolved in the sterilized water.

Next, ethanol was added to the deposits and RNA were deposited with centrifugation at 12,000 rpm. Then, the deposits were rinsed three times with ethanol and were air-dried. RNA so produced were re-suspended with 3 ml of RNase-free water. Concentration of mRNA sample so obtained were about 0.3 μg/μl determined by absorbance at 260 nm.

(5-2) Preparation of DHFR cDNA

5'-sense primer (PD1) having the base sequence set out in SEQ. ID. NO:12 and 3'-anti-sense primer (PD2) having the base sequence set out in SEQ. ID. NO:13 respectively were synthesized to amplify the gene of DHFR.

5'-end is a sequence artificially combined PstI site with the nonsense pyrimidine sequence of "TCCCTC", while 3'-end is a sequence extended from the termination codon to the BglII site which is about 85b downstream therefrom. 10 μl of solution containing 2 μg whole RNA was used to synthesize cDNA. Into the sterilized RNase-free tubes, 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP dCTP, dGTPs dTTP), 0.25 μl of acetylated BSA (4 mg/ml), 2.0 μg of oligo-dT-primer, 0.5 μl of PCR reverse transcriptase (200 units/μl) and 0.5 μl of RNase-free DEPC water were added. These were incubated at 37° C. for 60 minutes, and the reaction was terminated by heating it at 70° C. for 15 minutes, cDNA so produced were directly added to the reaction solution for PCR prepared previously. To this solution, 100 pmole of PD1 primer and PD2 primer respectively were added, then, 2.5 μl (0.5 μl) of Taq polymerase (Takara Shuzo), 20 μl of PCR Buffer (250 mM Tris.HCl (pH 8.3 at 25° C.), 375 mM KCl 15 mM $MgCl_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, and were adjusted with the sterilized water to make its final volume 100 μl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20 U (1 μl) of the restriction enzyme PstI as well as 20 U (1 μl) of the restriction enzyme BglII and 7 μl of the sterilized water were added and it was reacted at 37° C. for one hour. The reaction solution was then applied to an electrophoresis employing 0.8% agarose-gel at 50 mA for 30 minutes. Approximately 0.65 kb band was detected by exposuring it to the ultraviolet rays of 360 nm wavelength and was excised therefrom. These agarose fragments were poured into 1.5 ml tubes, then the tubes were centrifuged al 15,000 rpm for 10 minutes, and DNA solution was obtained by separating the solution using pipet.

(5-3) Preparation of Plasmid pSVP(D)S/DHFR

Plasmid pSVP(D)S-1 was partially digested with the restriction enzymes PstI and BamHI (this treatment is due to the presence of one PstI site in SV40 polyA). 0.5 μl of DHFR DNA solution was added to 0.1 μl (1 ng DNA) of this solution, 5'-end thereof is bond with PstI, while 3'-end thereof is bond with the projected ends of BamHI and BglII. At this moment, 2.0 μl of solution I attached to DNA ligation kit Ver.2 (Takara Shuzo) were added thereto, and these were reacted at 16' for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids additionally inserted thereinto DNA of DHFR as well as the restriction site for ApaI were selected and designated them as Plasmid pSVP(D)S/DHFR.

Figure 7:
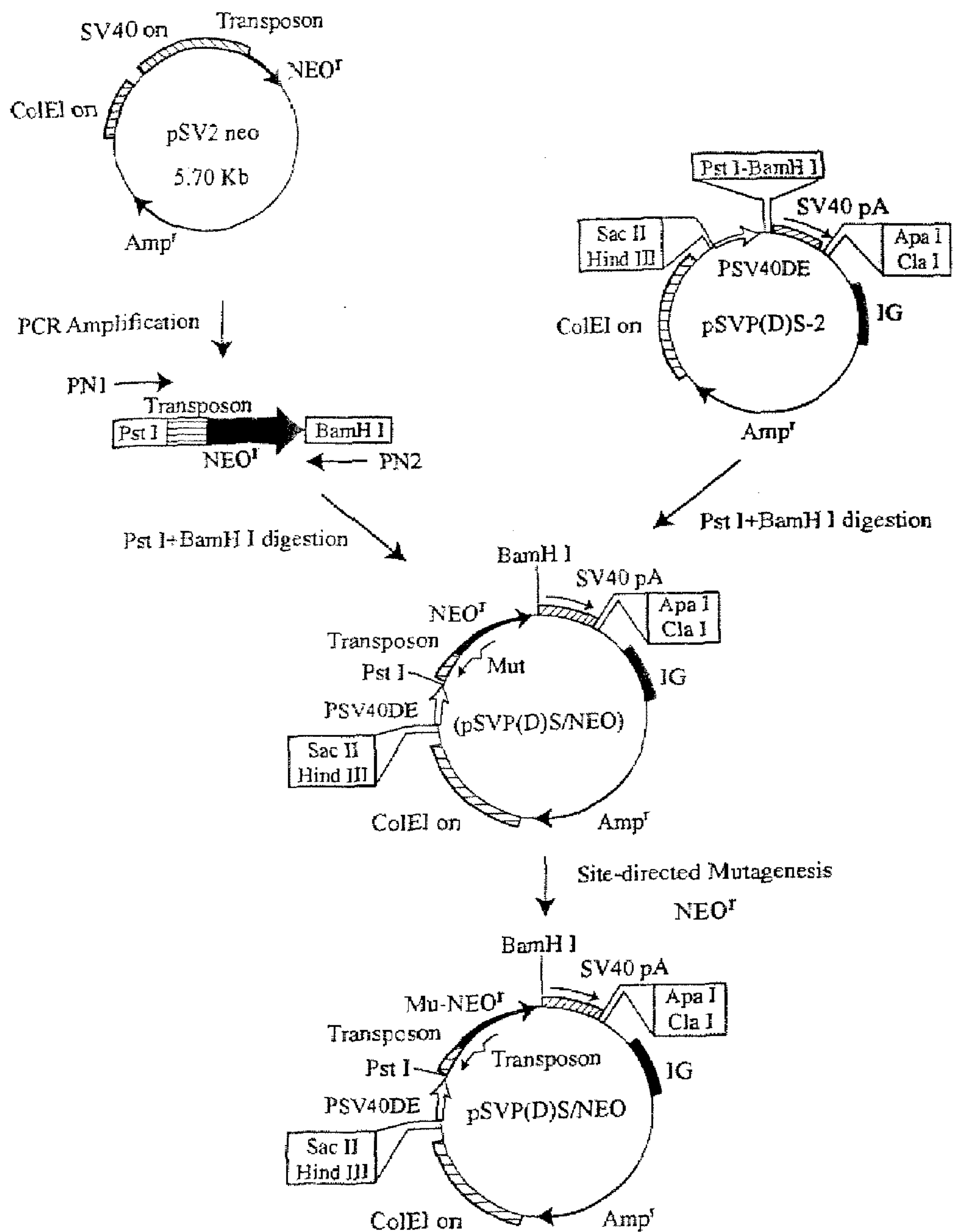
FIG. 7 shows a preparation scheme of Plasmid pSVP(D) S/NEO.

(6) Preparation of Plasmid pSVP(D)S/NEO (FIG. 7)

For Neomycin Phosphotransferase Gene (NEO gene) region, a sequence conjugated NEO gene translation region with the transposon sequence of 354 bases at 5'-upstream was used. This sequence is from Tn5 and is contained in pSV2-neo (J. Mol. Appl. Genet., p. 1327 (1982)), therefore, this was prepared by excising it from pSV2-neo. Firstly, 5'-sense primer (PN1) having the base sequence set out in SEQ. ID. NO: 14 and 3'-anti-sense primer (PN2) having the base sequence set out in SEQ. ID. NO:15 respectively were synthesized. 5'-end of PN1 primer have PstI site instead of HindIII site in the original sequence. Then, 3'-end of PN2 primer have BamHI site instead of SmaI site in the original sequence.

To 1 ng (0.1 μl) of pSV2-neo genome, 100 pmole of PN1 primer and PN2 primer respectively were added, then, 2.5 U (0.5 μl) of Taq polymerase (Takara Shuzo), 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, and were adjusted with the sterilized water to make its final volume 100 μl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20 U (1 μl) of the restriction enzyme PstII as well as 20 U (1 μl) of the restriction enzyme BamHI and 7 μl of the sterilized water were added and it was reacted at 37° C. for one hour. The reaction solution was then applied to an electrophoresis employing 0.8% agarose-gel at 50 mA for 30 minutes. Approximately 1.3 kb band was detected by exposuring it to the ultraviolet rays of 360 nm wavelength and was excised therefrom.

These agarose fragments were poured into 1.5 ml tubes, then the tubes were centrifuged at 15,000 rpm for 10 minutes, and DNA solution was obtained by separating the solution so produced with a pipet.

Plasmid pSVP(D)S-2 was partially digested with the restriction enzymes PstI and BamHI (this treatment is due to the presence of one PstI site in SV40 polyA). 0.5 μl of DNA solution of NEO gene were added to 0.1 μl (1 ng DNA) of this solution, thereby, PstI site and BamHI site were ligated.

With respect to this reaction, 2.0 μl of solution I attached to DNA ligation kit Ver.2 (Takara Shuzo) were added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto DNA of transposon sequence containing NEO gene were selected with regard to G418 resistance.

Further, anti-sense primer for introducing mutation which have the base sequence set out in SEQ. ID. NO:16 was synthesized to alter the base of "A" to "C" wherein the base "A" is immediately next to the initiation codon "ATG" in NEO gene translation region. 100 pmole of this anti-sense primer was added to 1 ng (1 μl) of pSVP(D)S/NEO genome, and was site-directed mutated by PCR in vitro Mutagenesis Kit (Takara Shuzo).

2.5 U (0.5 μl) of Taq polymerase (Takara Shuzo), 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, and were adjusted with the sterilized water to make its final volume 100 μl. One drop of the mineral oil (Sigma Chemical) was added to these mix solution, then PCR was performed according to the following condition.

Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Plasmid vector so produced was designated as Plasmid pSVP(D)S/NEO.

(7) Preparation of Plasmid PEXP-BL2

Figure 8:
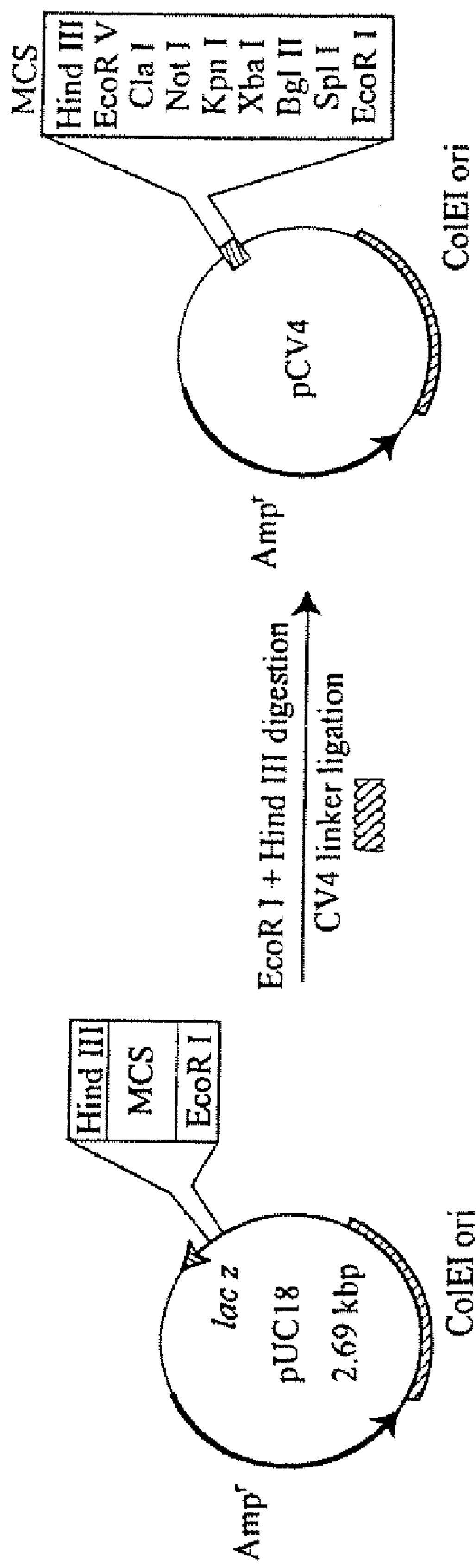
FIG. 8 shows a preparation scheme of Plasmid pCV4.

(7-1) Preparation of Plasmid pCV4 (FIG. 8)

Sense DNA having the base sequence set out in SEQ. ID. NO:17 and anti-sense DNA having the base sequence set out in SEQ. ID. NO:18 respectively were synthesized as a linker (CV4 linker) for Multi-Cloning Site to remove the Multi-Cloning site of Plasmid pUC18 (Takara Shuzo) and additionally incorporate thereinto Multi-Cloning Site (MCS) related gene.

Sequences at a site to be restricted by the restriction enzymes in this linker is 3'-HindIII-EcoRV-ClaI-NotI-KpnI-XbaI-BalII-SplI-EcoRI-5'. 1 ng (0.1 μl) of Plasmid pUC18 was treated with the restriction enzymes of HindIII and EcoRI.

Into the solution containing the plasmids so produced, 100 pmole of sense DNA and anti-sense DNA respectively for CV4 linker were added, then 2.0 μl of solution I attached to DNA ligation kit Ver.2 (Takara Shuzo) were further added, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight cultured at 37° C., of the plasmids collected from the colonies so produced, plasmids inserted thereinto DNA of CV4 linker were selected and designated them as vector pCV4.

Figure 9:
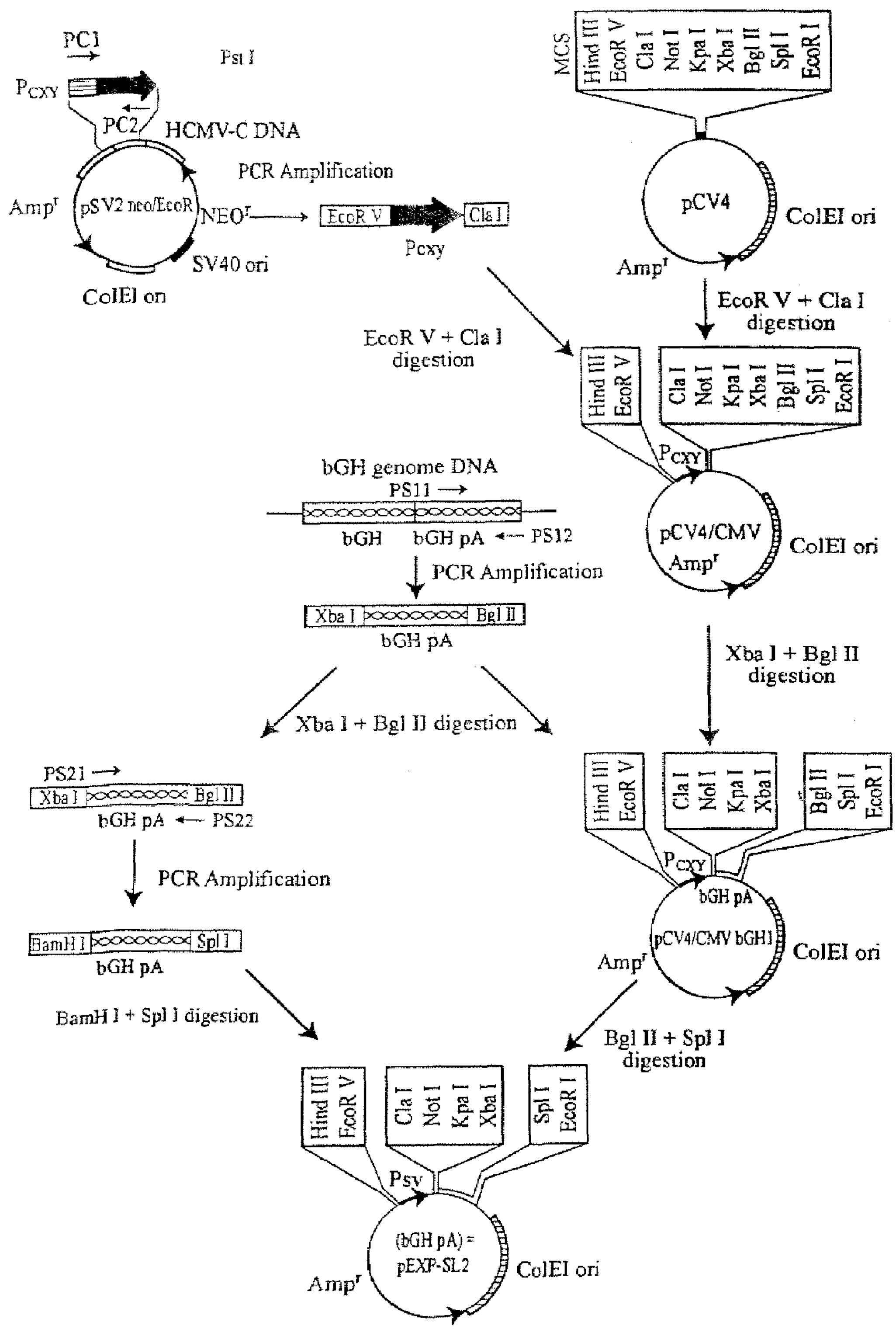
FIG. 9 shows a preparation scheme of Vector pEXP-BL2.

(7-2) Preparation of PCMV (FIG. 9)

5'-sense primer (PC1) having the base sequence set out in SEQ. ID. NO:19 and 3'-anti-sense primer (PC2) having the base sequence set out in SEQ. ID. NO:20 respectively were synthesized to excise PCMV from plasmid pSV2-neo/EcoH (obtained from Tokai University) prepared by incorporating the approximately 6 kb sequence containing the promoter/enhancer region of hCMV MIE antigen into pSV-Neo. 5'-end of PC1 primer have restriction site of EcoRV, while 3'-end of PC2 primer have ClaI site. To 1 ng (0.1 μl) of the plasmid pSV2-neo/EcoH genome, 100 pmole of PC1 primer and PC2 primer respectively, 2.5 U (0.5 μl) of Taq polymerase (Takara Shuzo), 20 μl of PCR Buffer (250 mM Tris-HCl (pH 8.3 at 25° C.), 375 mM KCl, 15 mM $MgCl_2$). 1.0 μl of 100 mM DTT, 0.5 μl of 10 mM dNTP (10 mM dATP, dCTP, dGTP, dTTP) and 0.25 μl of acetylated BSA (4 mg/ml) were added, then were adjusted with the sterilized water to make its final volume 100 μl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20 U(1 μl) of the restriction enzyme EcoRV as well as 20 U (1 μl) of the restriction enzyme ClaI and 7 μl of the sterilized water were added and it was reacted at 37° C. for one hour.

The reaction solution was then applied to an electrophoresis employing 0.8% agarose-gel at 50 mA for 30 minutes. Approximately 0.6 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet.

(7-3) Insertion of PCMV into Plasmids 1 ng (0.1 μl) of Plasmid pCV4 were treated with the restriction enzymes of EcoRV and ClaI, then 0.5 μl of PCMV DNA solution was added, and it was ligated to between EcoRV site and ClaI site. Into this reaction, 2.0μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by beat-shock at 42° C. for 60 seconds. It had been left on ice for 2 minutes. 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto PCMV DNA were selected and designated them as pCV4/CMV.

(7-4) Isolation of DNA having bGH polyA

While cell tissues obtained from bovine liver were sliced on the dry ice, they were extracted with the buffer (150 mM NaCl, 10 mM Tris-HCl (pH 8.0), 10 mM EDTA, 0.1% SDS) containing Proteinase K solution adjusted its concentration to be 100 μg/ml and were mixed gently. After one hour incubation at 55° C., they wore further incubated overnight at 37° C. Then, equivalent amount of the neutral phenol equilibrated with Tris were added thereto and they were mixed gently at the room temperature for 20 minutes.

After the centrifugation at 2,000×g under the room temperature for 10 minutes, the upper layer (5 ml) so separated was collected, then the collected layers were transferred to the fresh tubes, and they were centrifuged again under the same condition. Upper layer was collected again and was transferred to the fresh tubes, and they were re-centrifuged under the same condition. Upper layer thereof was collected again and was transferred to the fresh tubes, then, two times volume of 100% ethanol were overlayered thereon, and the buffer and ethanol were mixed with gentle agitation, DNA so produced were collected by rolling it with glass-stick then were air-dried, and 5 ml of TE solution was added thereto and it was dissolved at 4° C. overnight.

Concentration of DNA sample so obtained were about 0.5 μg/μl determined by absorbance at 260 nm.

(7-5) Insertion of bGH polyA into Plasmids

Two types of bGH polyA sequences, each of which have the different sites on the restriction enzymes, were prepared to doubly conjugate bGH polyA sequences. Firstly, two pairs of 5'-sense primer and 3'-anti-sense primer, namely, one pair of 5'-sense primer (PB11) having the base sequence set out in SEQ. ID. NO:21 and 3'-anti-sense primer (PB12) having the base sequence set out in SEQ. ID. NO:22, and the other pair of 5'-sense primer (PB21) having the base sequence set out in SEQ. ID. NO:23 and 3'-anti-sense primer (PB22) having the base sequence set out in SEQ. ID. NO:24 were synthesized.

bGH polyA sequences having at its both ends the desired sequences to be restricted by restriction enzymes were prepared from 100 ng of DNA sample so synthesized by using PCR template.

Firstly, to 100 ng (1 μl) of DNA sample, 100 pmole of sense primer PB11 and anti-sense primer PB12 respectively, 2.5 U (0.5 μl) of Taq polymerase (Takara Shuzo), 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, then were adjusted with the sterilized water to make its final volume 100 μl. One drop of the mineral oil (Sigma Chemical) was added to these mix solution, then PCR was performed according to the following condition.

Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20 U (1 μl) of the restriction enzyme XbaI as well as 20 U (1 μl) of the restriction enzyme BglII and 7 μl of the sterilized water were added and it was reacted at 37° C. for one hour.

The reaction solution was then applied to an electrophoresis employing 0.8% agarose-gel at 50 mA for 30 minutes. Approximately 0.23 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet.

Into 0.1 μl (1 ng DNA) of solution wherein Plasmid pCV4/CMV was treated with XbaI and BglII, 0.5 μl of DNA solution noted above were added, then 2.0 μl of solution I attached to DNA ligation kit Ver.2 (Takara Shuzo) were further added, and these were reacted at 16° C. for 30 minutes.

0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, 0.9 ml of SOC medium (Toyobo) was added thereto and was cultured by shaking it with a shaker at 37° C. for one hour.

The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto bGH polyA DNA were selected and designated them as pCV4/CMV-bGH1.

(7-6) Preparation of Vector pEXP-BL2

To 1 ng of DNA sample prepared through PCR amplification from Primers PB11 and PB12, 100 pmole of sense primer PB21 and anti-sense primer PB22 respectively, 2.5 U (0.5 μl) of Taq polymerase (Takara Shuzo). 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, then were adjusted with the sterilized water to make its final volume 100 μl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20 U (1 μl) of the restriction enzyme BamHI as well as 20 U (1 μl) of the restriction enzyme SplI and 7 μl of the sterilized water were added and it was reacted at 37° C. for one hour. The reaction solution was then applied to an electrophoresis employing 0.8% agarose-gel at 50 mA for 30 minutes. Approximately 0.47 kb band was detected by exposuring it to the ultraviolet rays of 360 nm wavelength and was excised.

These agarose fragments were poured into 1.5 ml tubes, then the tubes were centrifuged at 15,000 rpm for 10 minutes, and DNA solution was obtained by separating the solution so produced with a pipet.

Into 0.1 μl (1 ng DNA) of solution wherein Plasmid pCV4/CMV-bGH1 was treated with BglII and SplI, 0.5 μl of DNA solution noted above were added, then 2.0 μl of solution I attached to DNA ligation kit Ver.2 (Takara Shuzo) were further added, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 g/ml ampicillin respectively. After the overnight culture at 37° C., of the plasmids collected from the colonies so produced, plasmids inserted thereinto the second bGH polyA DNA, namely, plasmids ($(\text{bGH polyA})^2$) inserted thereinto and doubly bond to bGH polyA DNA were selected and designated them as cassette vector PEXP-BL2 having MCS cistron.

Figure 10:
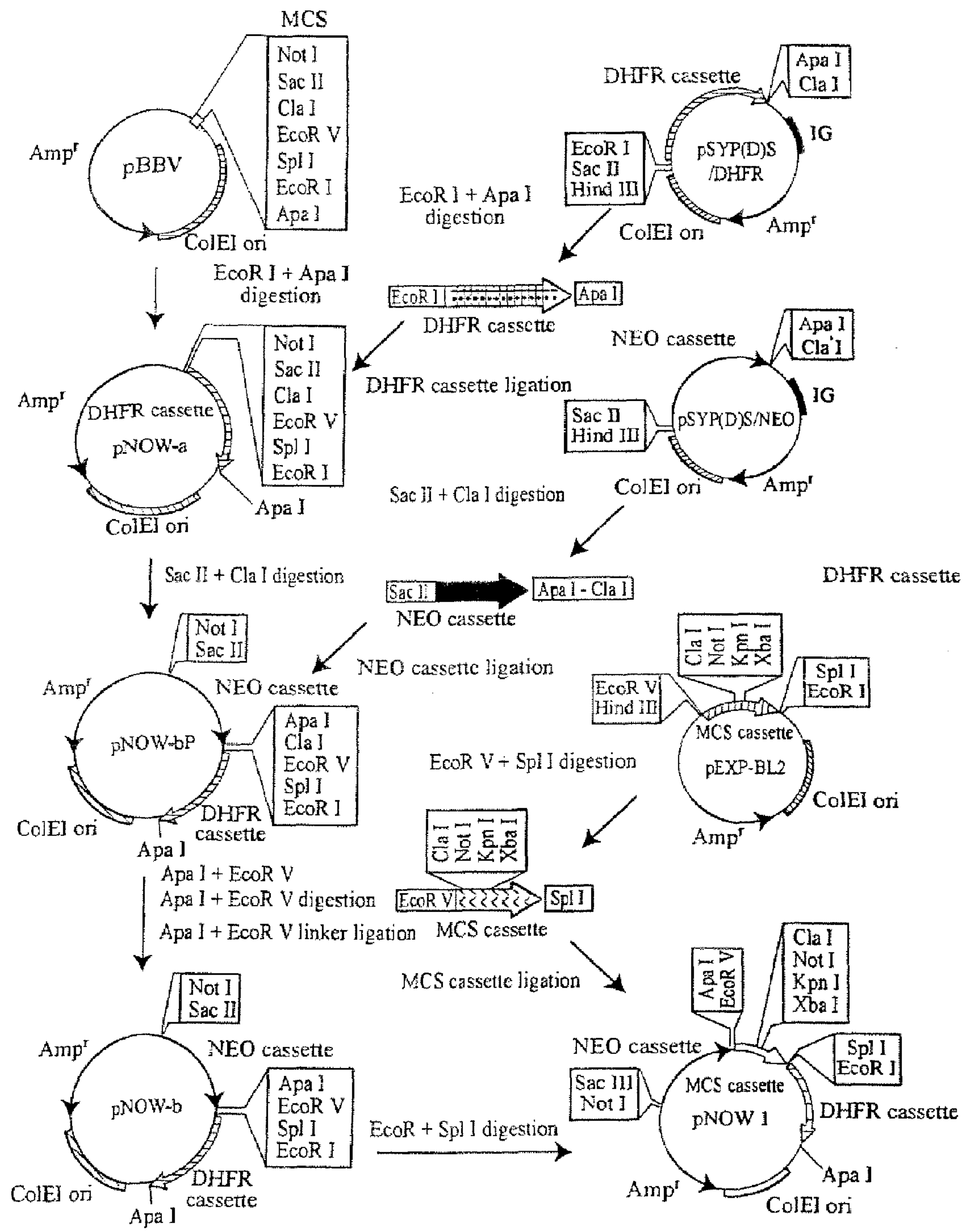
FIG. 10 shows a preparation scheme of Plasmid pNOW1.

(8) Preparation of Plasmid pNOW1 (FIG. 10)

(8-1) Preparation of Plasmid pNOW-a

To 100 ng (1 μl) of Plasmid pSVP(D)S/DHFR, 1 μl of 10×H solution was added, then, 20 U (1 μl) of the restriction enzyme EcoRI and 20 U (1 μl) of the restriction enzyme ApaI were further added, and these were reacted at 37° C. for one hour. The reaction solution was then applied to an electrophoresis employing 0.8% agarose-gel at 50 mA for 30 minutes. Approximately 1.75 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet. This DNA sequence constituted DHFR gene cistron and was consisted of $P_{sV_{40}DE}$. Mu-DHFR (mutated) gene and SV40 polyA.

On the other hand, 1 ng (1 μl) of Plasmid pBBV to be inserted thereinto DNA sequence which constitutes DHFR gene cistron were treated with the restriction enzyme EcoRI and ApaI. 0.5 μl of solution containing DNA sequence which constitutes DHFR gene cistron were added to the solution containing the Plasmids so prepared, thereby, it was ligated between EcoRI and ApaI site. Into this reaction, 2.0 μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively.

After the overnight culture at 37° C., of the plasmids collected from the colonies so produced, plasmids additionally inserted thereinto DNA which constitutes DHFR gene cistron were selected and designated them as pNOW-a.

(8-2) Preparation of Plasmid pNOW-bp

To 100 ng (1 μl) of Plasmid pSVP(D)S/NEO, 1 μl of 10×H solution was added, then, 20 U (1 μl) of the restriction enzyme SacII and 20 U (1 μl) of the restriction enzyme ClaI were further added, and these were reacted for one hour. The reaction solution was then applied to an electrophoresis employing 0.8% agarose-gel at 50 mA for 30 minutes. Approximately 2.4 kb band was detected by exposuring it to the ultraviolet rays of 360 nm wavelength and was excised.

These agarose fragments were poured into 1.5 ml tubes, then the tubes were centrifuged at 15,000 rpm for 10 minutes, and DNA solution was obtained by separating the solution so produced with a pipet. This DNA sequence constituted NEO gene cistron and was consisted of pSV4 ODE, transposon sequence, Mu-NEO (mutated) gene and SV40 polyA.

On the other hand, 1 ng (1 μl) of Plasmid pNOW-a to be inserted thereinto DNA sequence which constitutes NEO gene cistron were treated with the restriction enzyme SacII and ClaI. 0.5 μl of solution containing DNA sequence which constitutes NEO gene cistron were added to the solution containing the plasmids so prepared, thereby, it was ligated between SacII and ClaI site. Into this reaction, 2.0 μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heal-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids additionally inserted thereinto DNA which constitutes NEO gene cistron were selected and designated them as pNOW-bp.

(8-3) Preparation of Plasmid pNOW-b

ClaI site was removed by substituting the newly synthesized ApaI-EcoRV linker for a serial sites of ApaI-ClaI-EcoRV to remove the ClaI site of multi-cloning site in Plasmid pNOW-bp so prepared. Firstly, as this linker, sense DNA having the base sequence of 5'-CGAT-3' and anti-sense DNA having the base sequence of 3'-CGGGCTA-5' were respectively synthesized. 1 ng (0.1 μl) of Plasmid pNOW-bp were digested with the restriction enzymes of ApaI and EcoRV. To the solution containing the plasmids so prepared, 100 pmole of ApaI-EcoRV linker sense DNA and anti-sense DNA respectively were added, then, 2.0 μl of solution I attached to DNA ligation kit Ver.2 (Takara Shuzo) were further added, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids additionally inserted thereinto DNA which constitutes NEO gene cistron were selected and designated them as pNOW-b.

(8-4) Preparation of Plasmid pNOW1

To 100 ng (1 μl) of Plasmid pEXP-BL2, 1 μl of 10×H solution was added, then. 20 U (1 μl) of the restriction enzyme EcoRV and 20 U (1 μl) of the restriction enzyme SplI were further added, and these were reacted for one hour. The reaction solution was then applied to an electrophoresis employing 0.8% agarose-gel at 50 mA for 30 minutes. Approximately 1.1 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet. This DNA sequence constituted MCS cistron and was consisted of $P_{CMV}$, MCS-B and (bGH polyA)$^2$.

On the other hand, 1 ng (1 μl) of Plasmid pNOW-b to be inserted thereinto DNA sequence which constitutes MCS cistron were treated with the restriction enzyme EcoRV and SplI. 0.5 μl of solution on DNA sequence which constitutes MCS cistron were added to the solution containing the plasmids so prepared, thereby, it was ligated between EcoRV and SplI site. Into this reaction, 2.0 μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C. of the plasmids collected from the colonies so produced, plasmids inserted thereinto DNA which constitutes MCS cistron were selected and designated them as pNOW1.

Structure of Plasmid pNOW1 is shown in FIG. 11. Then, whole base sequences of Plasmid pNOW1 is set out in SEQ. ID. NO:25.

EXAMPLE 2

Construction of Expression Vector pNOW1-hMBP

First of all, hMBP sequences from its initiation codon to its stop codon were amplified from human liver cDNA library (Clontech) with a zymoreacter (Alto) by using the primer having the base sequence of AAGGAAAAAAGCGGCCGCATGTCCCTGTTTCC ATCACTC (SEQ. ID. NO:26) and that having the base sequence of GCTCTAGATCAGATAGGGAACTCACAGAC (SEQ. ID. NO:27).

hMBP cDNA so obtained were digested with the restriction enzymes of NotI and XbaI, and cDNA corresponding to 66~812 bp in such cDNA (SEQ. ID. NO:2) so obtained were employed as an insert.

Figure 12:
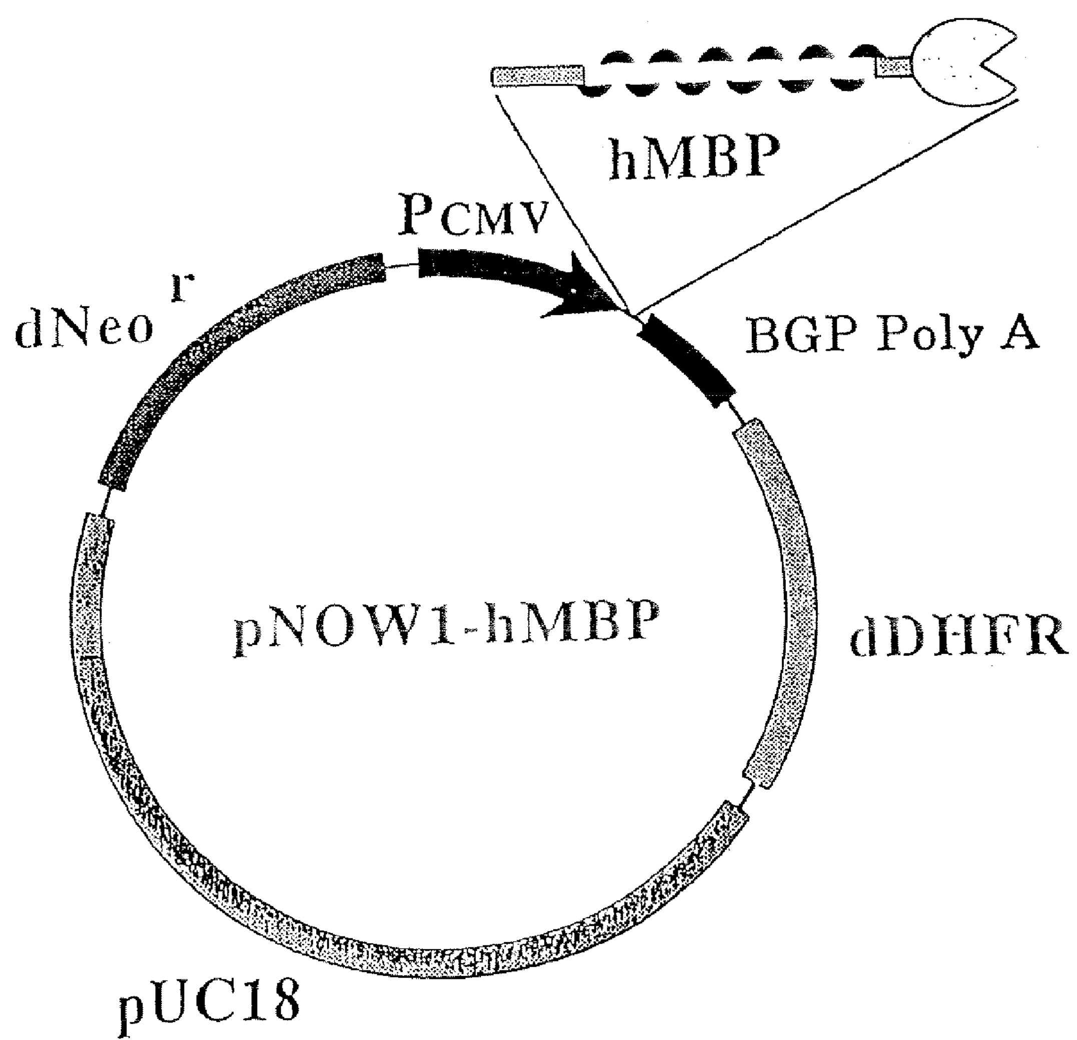
FIG. 12 is a schematic view on the structure of Plasmid pNOW1-hMBP.

Then, the expression vector pNOW1 prepared in Example 1 was digested with the restriction enzymes of NotI and XbaI, and said insert was inserted with DNA ligation kit (Takara Shuzo) into the downstream of cytomegalovirus promoter (pCMV), namely, between pCMV and BGP polyA (corresponding to (bGHpA)$^2$ in FIG. 11). The expression vector so prepared was designated as Plasmid pNOW1-hMBP, and its structure is illustrated as schematic view in FIG. 12.

EXAMPLE 3

Selection of Expression Clone (I) Introduction of Expression Vector pNOW1-hMBP into Chinese Hamster Ovary (CHO) Cells Lacking Dihydrofolate Reductase (dhfr$^-$)

Iscove's Modified Dulbecco's Medium (IMDM; GIBCO) not contained therein hypoxanthine and thymidine but supplemented thereto 10% bovine fetal serum (FCS, GIBCO) was prepared, then DG44 CHO cell strain lacking DHFR gene (dhfr$^-$) were mixed therewith to be the concentration of $1\times10^5$ cell/ml, and they were inoculated into the dishes of 60 mm diameter and were cultured for 24 hours under the condition of 37° C. and 5% $CO_2$. Culture supernatant was discarded, then IMDM containing 10% FCS were added to be 6 ml wherein IMDM contains 100 μl of solution prepared by mixing 5 μg of DNA (Expression Vector pNOW1-hMBP) with lypofectin solution (DOTAP Liposomal Transfection Reagent; Boehringer Mannheim), and Expression Vector pNOW1-hMBP was introduced into the host CHO cells of $dhfr^-$ by further adding thereto hypoxanthine (final concentration of 10 nm) (GIBCO) as well as thymidine (final concentration of 100 nM) (GIBCO) and culturing it for 16 hours. After then, culture supernatant was discarded, then 6 ml of IMDM supplemented therein 10% FCS, hypoxanthine and thymidine are added thereto, and the culture were continued for another 24 hours.

(2) Production of Neomycin (G418) Resistance CHO Cells

After 24 hours culture, the cells introduced thereinto the expression vector pNOW1-hMBP, such cells were treated with trypsin, then were collected from dishes, and were counted on the cell numbers, thereafter, cell suspension were inoculated (poured) into 10 pieces of 96-well microplate in the amount of 0.1 ml/well wherein the cell suspension is suspended by IMDM supplemented thereto 109% PCS and contained 400 μg/ml of Neomycin (G418) to be the concentration of $1\times10^5$ cell/ml. When the culture had been continued for two weeks under the condition at 37° C. and 5% $CO_2$. 84 wells of 960 wells have active cells, and there were G418 resistance cells (clones).

When the productivities of hMBP by such G418 resistance clones were studied, most of G418 resistance clones exhibit high productivity on hMBP.

Figure 13:
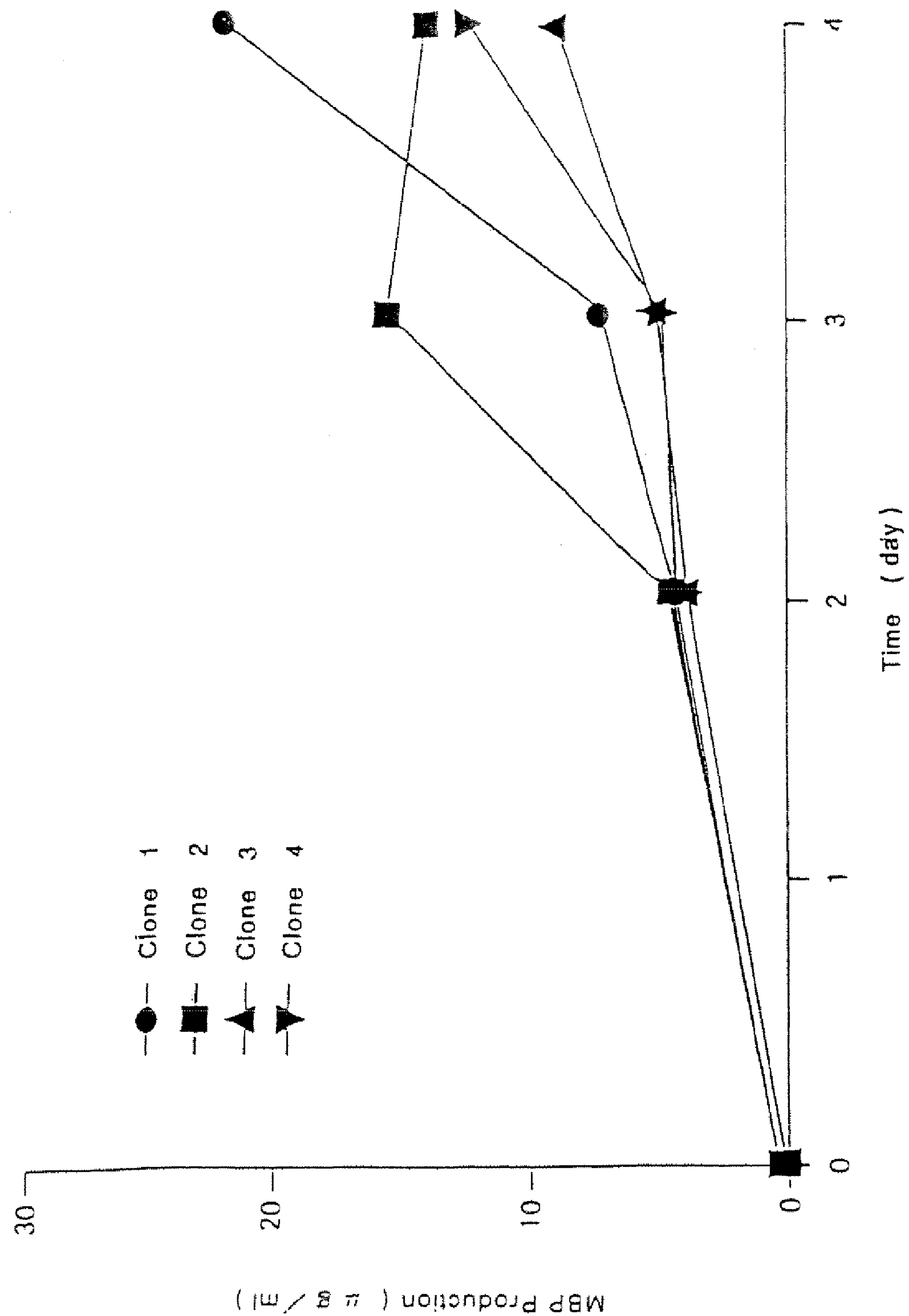
FIG. 13 is a graph showing production of rhMBP in the neomycin (G418) resistance clone.

Some clones were selected from the clones having the demonstarated hMBP productivities and were inoculated into 25 $cm^2$ culture flask. Cultivation were continued until density of the cells were increased, and the cell number measured at that moment was $3\times10^6$ cells/25 $cm^2$ culture flask. Culture supernatant from each of culture flasks were discarded, then 2 ml of IMDM supplemented thereto 10% FCS were added thereto wherein components of such IMDM were identical to IMDM previously noted, and culture were performed for four days, thereafter, culture supernatant so obtained were collected. When amount of hMBP (rhMBP) in the collected culture supernatant were measured, there were production of over 5 μg/ml in some culture flasks. Amounts of hMBP were quantified with regard to the native MBP as a control, anti-rabbit polyclonal antibody (expressed in *Escherichia coli*) for carbohydrate recognition domain (CRD) and neck region in the collectin and hMBP (subjects to be quantified), along with the method of Suzuki et al., (Y. Suzuki, et al., "Characterization of Recombinant Bovine Conglutinin Expressed in a Mammalian Cell". *Biochem. Biophys. Res. Commun.,* 238, pp. 856-863 (1997)). Results on four clones having high productivities are shown in the graph of FIG. 13. hMBP production by the clone having the highest productivity was 23.3 μg/ml.

(3) Production of MTX Resistance CHO Cells

After stabilizing the hMBP production clones by further subculturing them, gene amplification was performed with a medium supplemented thereto the low concentration MTX.

Firstly, each of the selected two cell clones were mixed with IMDM supplemented thereto 10% dialyzed FCS (JRH Bioscience) and contained 5 nM MTX and 400 μg/ml of Neomycin (G418), thereafter, amount of 0.1 ml/well of which were inoculated (poured) into 10 pieces of 96-well microplate When the culture had been continued for two weeks under the condition at 37° C. and 5% $CO_2$, most of 960 wells have active cells, and there were 5 nM MTX resistance cells (clones). When the productivities of hMBP by such 5 nm MTX resistance clones were studied, most of 5 nM MTX resistance clones exhibit high productability on hMBP. Five clones were optionally selected from such clones, then each of which were inoculated into 25 $cm^2$ culture flasks, and the culture were continued until density of the cells were increased.

Figure 14:
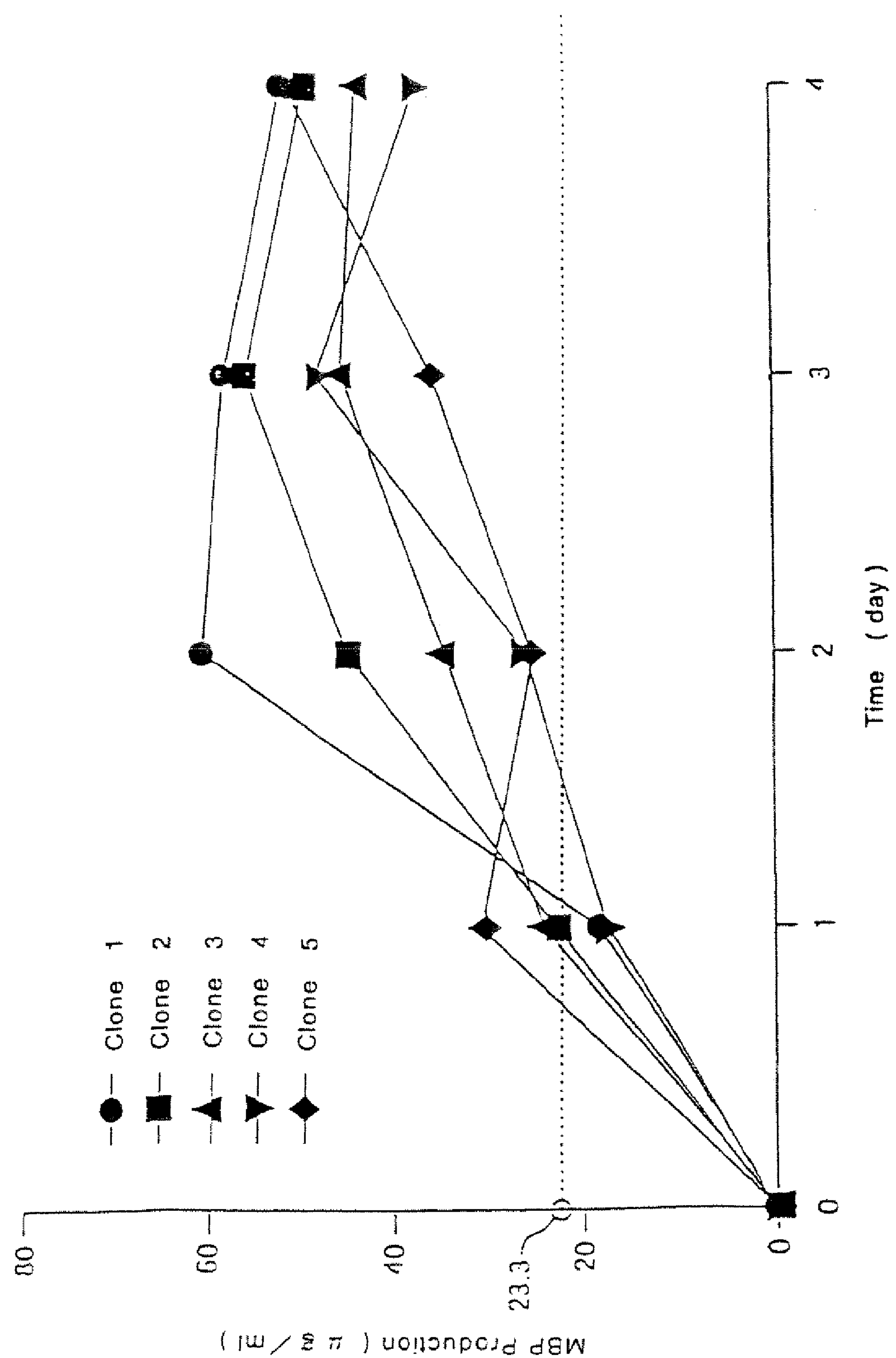
FIG. 14 is a graph showing production of rhMBP in the MTX resistance clone.

Culture supernatants were discarded, then 2 ml of IMDM (supplemented thereto 5 nM MTX and 400 μg/ml of G418) were added thereto, and culture were performed for four days, thereafter, culture supernatant so obtained were collected and production level of hMBP were measured. Amounts of hMBP were quantified according to the similar method noted in Example 3(1). Results are shown in the graph of FIG. 14. hMBP production by the clone having the highest productivity was 54.1 μg/ml.

EXAMPLE 4

Analysis of Structure of rhMBP by PAGE Analysis and Gel-Filtration Chromatography (1) Purification of rhMBP The clone having the highest productivity in the clones so produced was inoculated into 225 $cm^2$ culture flask and was the culture were continued until density of the cells were increased. Then, the culture supernatants were discarded, then 50 ml of CHO-S-SFM II medium (vitamin C was added to be the final concentration of 100 mM if it is added) containing 5 nM MTX and 400 μg/ml of G418 were added thereto, and culture were performed for four days. Culture supernatant so obtained were collected and was dialyzed to TBS (prepared from TBS powder (Takara Shuzo)), thereafter, it was dialyzed to TBSC (5 mM $CaCl_2$. TBS).

Next, it was purified by mannan-agarose (SIGMA). Namely, mannan-agarose were packed in column (Column PD-10, Empty, Pharmacia), then the dialyzed culture solution were passed therethrough, were washed with TBSC and were eluted with TBSE (10 mM EDTA, TBS). After such elution, 1M $CaCl_2$ were added thereto to be its final concentration of 15 mM, then the solution were applied again to the mannan-agarose, then were washed with TBSC and were eluted with TBS containing 100 mM mannose, thereafter, the purified rhMBP products were produced by re-dialyzing such re-eluted solution to TBSC.

Figure 15:
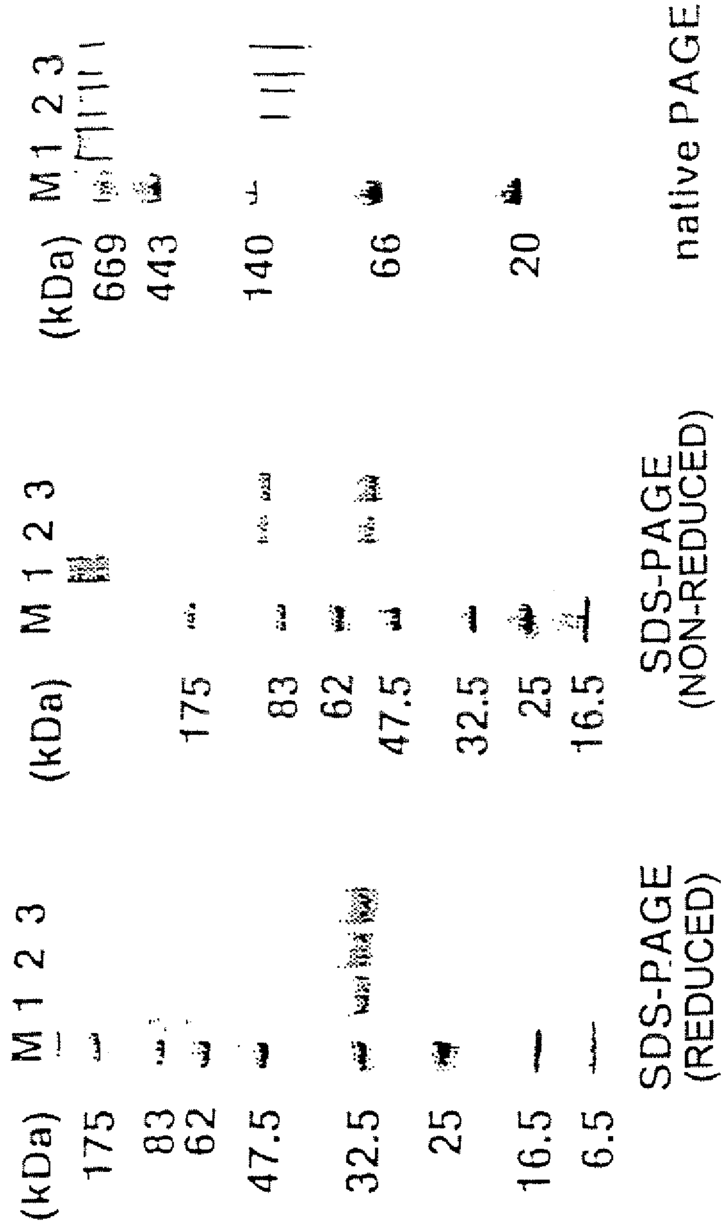
FIG. 15 shows results of PAGE analysis on rhMBP.

(2) PAGE Analyse of Purified rhMBP hMBP produced in Example 4(1) were analyzed by PAGE. SDS-PAGE employed polyacrylamide gel (Daiichi Pure Chemical) having the concentration gradient of 4~20% under the non-reducing condition, polyacrylamide gel (Daiichi Pure Chemical) having the concentration gradient of 10~20% under the reducing condition and polyacrylamide gel (Daiichi Pure Chemical) having the concentration gradient of 4~20% for the native PAGE. Polypeptides were stained with 1% Coomassie Blue (CBB). Results thereof are shown in FIG. 15. In FIG. 15, Lane M is the molecular weight marker (prestained protein marker broad range (NEW ENGLAND BIO Labs)), Lane 1 is the native hMBP, Lane 2 is rhMBP (cultured with vitamin C) and Lane 3 is rhMBP (cultured without vitamin C).

As shown in FIG. 15, although there was band at the molecular weight which is same to the native hMBP on SDS-PAGE under the reduction condition, there were bands pattern of which are different from those of the native hMBP on SDS-PAGE under the non-reducing condition and the native PAGE.

(3) Gel-Filtration Chromatography Analysis of Purified rhMBP

Purified rhMBP were gel-filtrated with SUPEROSE™ 6 HR10/30 medium (ø10 mm×300 mm length; Pharmacia) at flow rate of 0.5 ml/min using 20 mM Tris-HC1 (pH 8.0), 0.15 NaCl, 5 mM EDTA. 40 μg of rhMBP was applied on this column and was measured at 280 nm absorbance.

Figure 16:
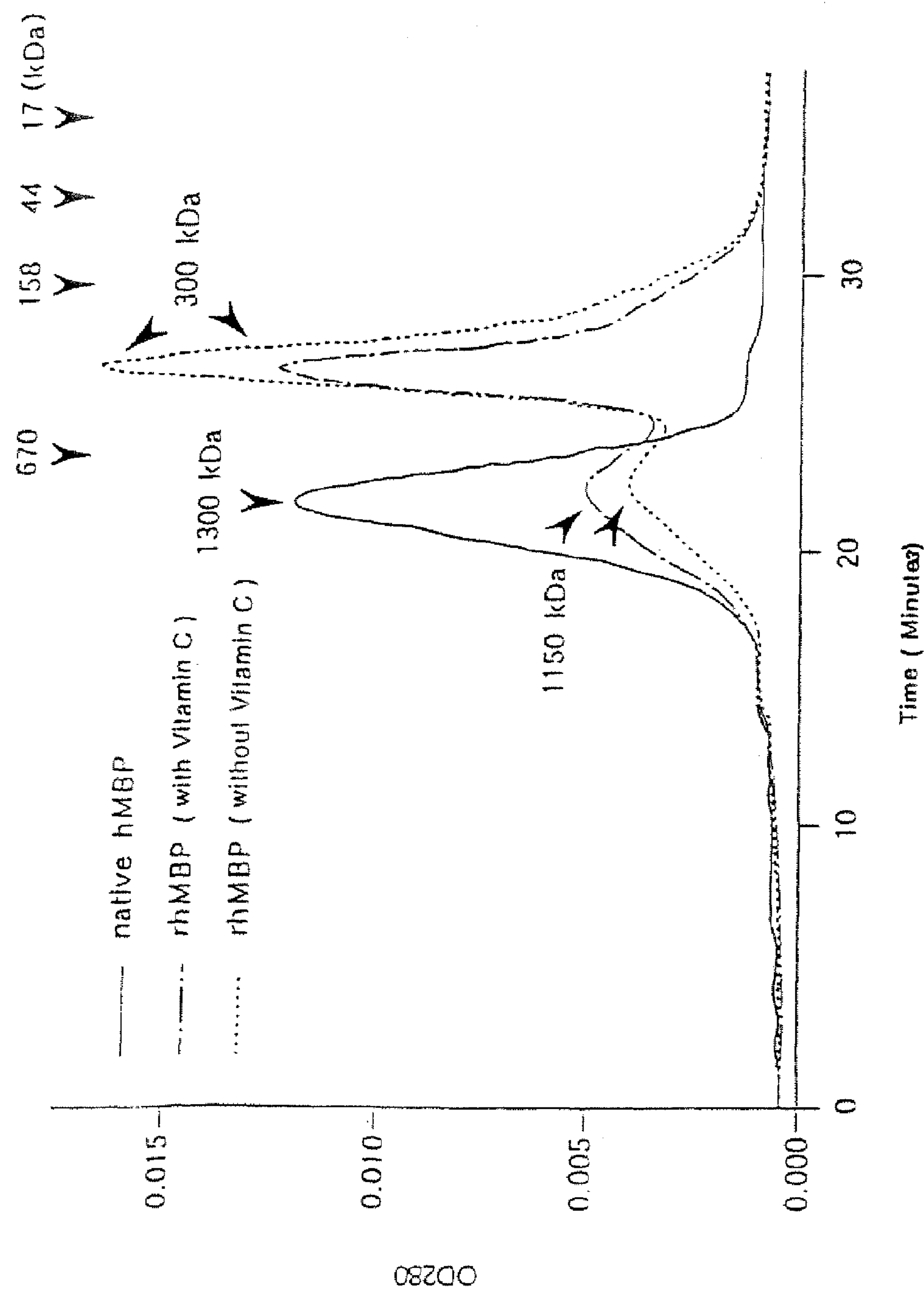
FIG. 16 is a graph showing results of gel-filtrations on rhMBP.

Gel-Filtration Standard (thyroglobulin (670 kDa), bovine γ-globulin (158 kDa), chicken ovalbumin (44 kDa), bovine myoglobulin (17 kDa) Bio-Rad) were employed for calibration of the column. As shown in FIG. 16, there were major peaks at 300 kDa in rhMBP and at 1,300 kDa in the native hMBP.

EXAMPLE 5

Sugar Binding Activities and Sugar Binding Specificities by rhMBP and Native hMBP Microtiter Plates were treated with 100 μl of coating buffer (15 mM sodium carbonate, 35 mM sodium hydrogen carbonate, 0.05% sodium azide, pH 9.6) containing mannan (10 μg/ml:SIGMA) at 4° C. overnight. After each treatment step, the plates were washed three times with TBSNTC solution (TBS, 0.05% sodium azide, 0.05% TWEEN 20 (Registered Trade Mark), 5 mM calcium chloride). After completing the coating of the plates, the plates were treated and blocked with BLOCKACE™ blocking solution (Dainippon Pharmaceutical) at room temperature for one hour.

After washing them, samples of stepwise dilution of the native hMBP, rhMBP (cultured with vitamin C), rhMBP (cultured without vitamin C) having the concentration of 200, 100, 50, 25, 12.5, 6.25 ng/ml, combination samples of 200 ng/ml of each hMBP with EDTA added to be its concentration of 10 mM, and combination samples of 50 ng/ml of each hMBP with mannose added to be its concentration of 100 mM were prepared, thereafter, 100 μl of each of them were poured into each well and were incubated at 37° C. for one hour. After washing them, biotinylated anti-rabbit anti-hMBP antibody (biotinylated with EZ-Link (Registered Trade Mark) Sulfo-NHS-LC-Biotin (PIACE)) diluted 1,000 times with TBSNTC were added thereto, then they were incubated at 37° C. for one hour and were washed. Then, a complex of avidin and biotinylated alkaline phosphatase was formed at 37° C. for 30 minutes with VECTASTAIN ABC-AP STANDARD KIT (VECTOR) and was washed. Finally, 100 μl of TMB substrate solution (TMB Microwell Peroxidase Substrate System: KPL) were added to each well. After incubating them at room temperature for 30 minutes, 100 μl of 1M phosphoric acid were added thereto, and their absorbance were measured at 450 nm (Model 450 Microplate Reader; Bio-Rad). Then, evaluation on sugar inhibiting activities were performed according to the method of Lu et al., (Biochem. J., Vol. 284, pp. 795-802 (1992)) employing this ELISA system.

After coating the microtiter plates with mannan (100 μg/μl well), the native hMBP and rhMBP (cultured with or without vitamin C) were reacted under the co-presence of the sugars in their final concentration of 100, 50, 25, 12.5, 6.3, 3.1, 1.6 mM. Sugar binding specificity was indicated as I so with regard to sugar concentration necessary to halve binding activities in comparison with the suppression curve. Results thereof are shown in the following Table 1.

TABLE 1

Sugar Binding Specificities on rhMBP and native hMBP

| | $I_{50}$(mM)* | | |
|---|---|---|---|
| Sugars | native hMBP | rhMBP (with Vitamin C) | rhMBP (without Vitamin C) |
| N-Acetyl-D-Glucosamine | 2.7 | 3.6 | 3.8 |
| L-Fucose | 4.2 | 4.4 | 8.7 |
| D-Fucose | 33.5 | 39.1 | 86.7 |
| D-Mannose | 3.7 | 6.7 | 6.8 |
| Maltose | 7.4 | 6.4 | 7.4 |
| N-Acetyl-D-Mannosamine | 4.4 | 6.9 | 6.9 |
| Glucose | 3.2 | 2.0 | 2.4 |
| Galactose | 24.2 | 29.8 | 36.7 |
| N-Acetyl-D-Galactosamine | >100 | >100 | >100 |
| Lactose | 36.0 | 46.6 | 59.4 |

*Sugar concentration to halve binding activities with mannan

Figure 17:
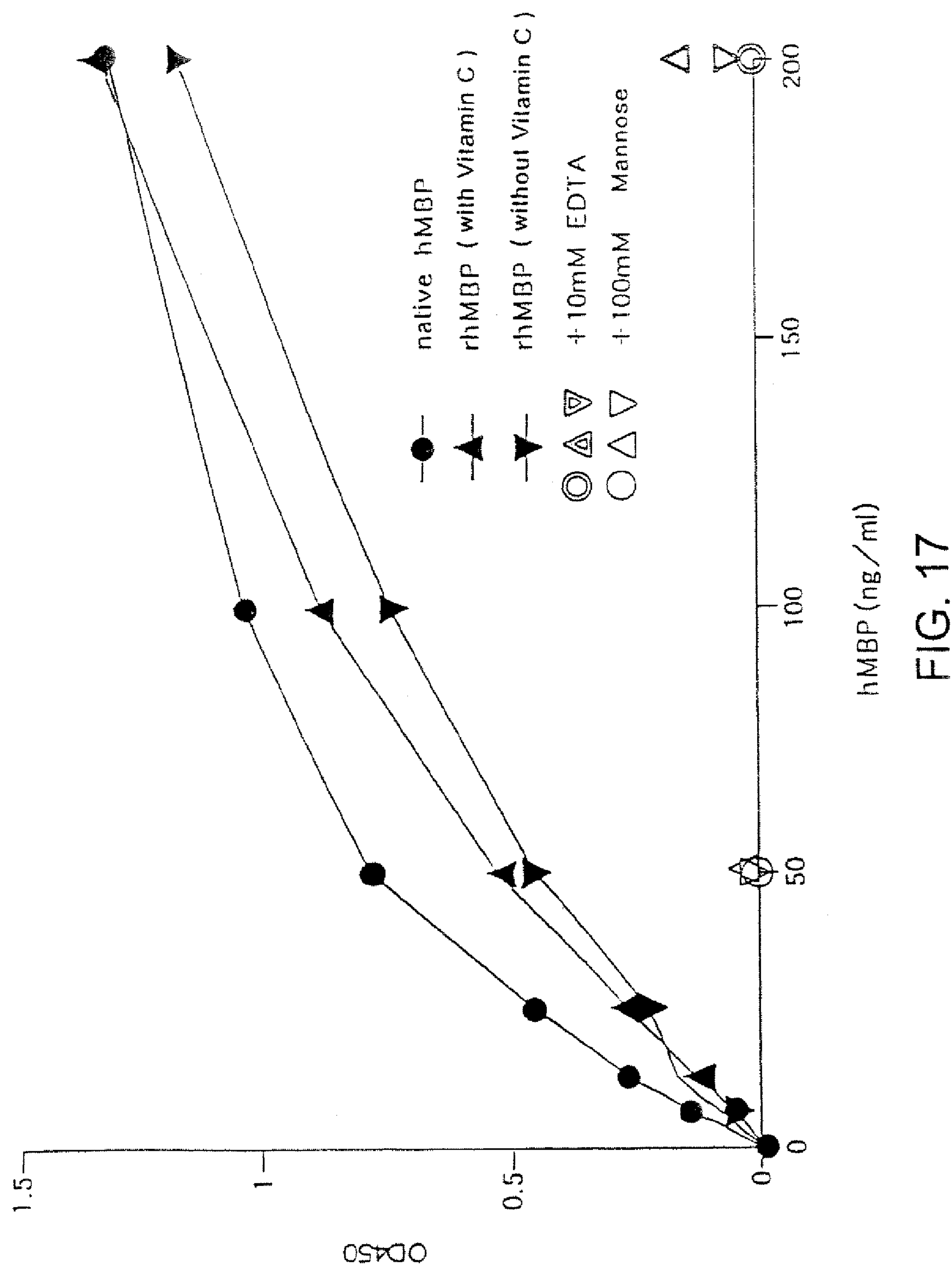
FIG. 17 is a graph showing glyco-binding activities on rhMBP and native hMBP.

Apparently from the results shown in Table 1, sugar binding specificities by rhMBP are substantially identical to those by the native hMBP. Then, as shown in FIG. 17, sugar binding activity by rhMBP are similar to those by the native hMBP.

EXAMPLE 6

Hemagglutination Inhibition (HI) Activities (1) Viruses

Influenza A virus A/Ibaraki/1/90 ($H_3N_2$:Influenza A virus (A-Hong Kong)) were used to evaluate Hemagglutination Inhibition (HI) Activities.

Viruses were subcultured 40 times with CAM (chorioallantoic membrane) from the matured egg according to the standard method and were stored at −70° C. until use. As a growth medium for the viruses, Eagle MEM medium (Nissui Pharmaceutical) containing 3% vitamin for tissue culture, 0.2% albumin, 0.1% glucose and 0.2 ng/ml acetylated trypsin was used.

(2) Remagglutination Inhibition (HI) Activities by rhMBP

In accordance with the method of Okuno et al., (J. Clin. Microbiol., Vol. 28, pp. 1308-1313 (1990)), Hemagglutination Inhibition (HI) activities were determined. Namely, native hMBP and rhMBP (cultured with or without Vitamin C) (5 μg/ml) were diluted double-stepwise with 25 μl of TBSC on 96-well microplates. 25 μl of 16HAU (Hemagglutination Unit) virus solution were added to each of MBP solution diluted stepwise, then were reacted at 37° C. for 60 minutes, and 50 μl of 0.5% chicken's erythrocytes solution were added thereto. After the incubation at 4° C. for 60 minutes, effects on rhMBP against viral hemagglutination on chick's erythrocytes were observed. Results are shown in the following Table 2 and FIG. 18.

TABLE 2

Minimum Protein Concentration (ng/ml) for Hemagglutination Inhibition (HI) Activities by rhMBP and native hMBP

| | Minimum Protein Concentration (ng/ml) for HI Activities |
|---|---|
| native hMBP | 40 |
| rhMBP (with Vitamin C) | 80 |
| rhMBP (without Vitamin C) | 80 |

Figure 18:
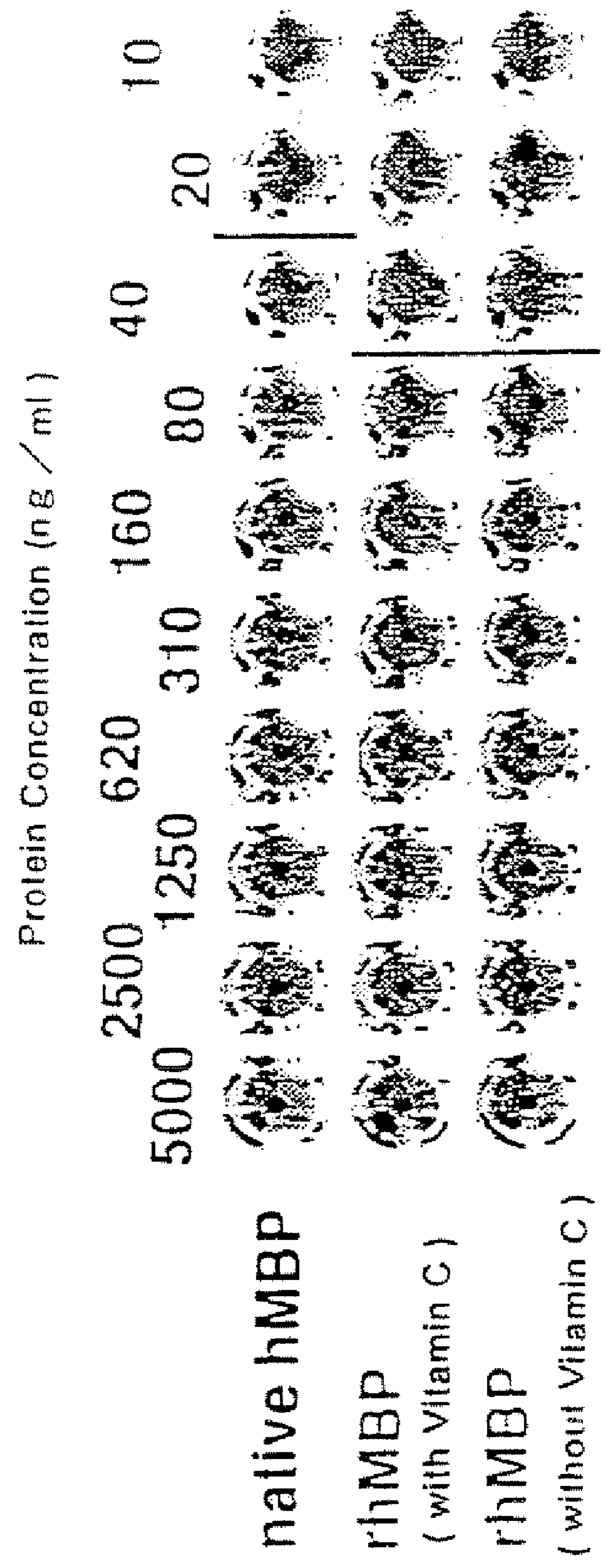
FIG. 18 shows activities by rhMBP on Hemagglutination Inhibition (HI).

Results shown in Table 2 and FIG. 18 indicated that Hemagglutination Inhibition (HI) activities by rhMBP are not inferior to that by native hMBP.

EXAMPLE 7

Neutralization Activities (1) Viruses

Influenza A virus A/Ibaraki/l/90 employed in Example 6 were used.

(2) Neutralization Activities

Neutralization Activities were evaluated according to the method of Okuno et al., (J. Clin. Microbiol., Vol. 28, pp. 1308-1313 (1990)). The native hMBP and rhMBP (cultured with or without vitamin C) were diluted double-stepwise with TBSC and were mixed equivalently with viral solution of 50 Focus Forming Unit (FFU)/25 μl, thereafter, they were reacted at 37° C. for 60 minutes. 50 μl of these reaction solution were inoculated into three wells per each concentration of MBP dilution on 96-well microplates wherein Madin-Darby Canine Kidney (MDCK) cells were monolayer cultured in Eagle MEM medium containing 10% bovine fetal serum (GIBCO). After incubating them at 35° C. for 60 minutes, cells were washed and were added thereto growth medium for influenza viruses containing 0.5% tragacanth gum (Wako Pure Chemical Industries), thereafter, they were cultured for 24 hours in $CO_2$ incubator.

After the culture, cells were washed and were fixed with ethanol. After air-drying the cells, they were reacted with each of anti-influenza hyperimmune rabbit serum, anti-rabbit IgG goat serum (ICN Pharmaceuticals) and peroxidase anti-peroxidase (rabbit) complex (ICN Pharmaceuticals) at 37° C. for 30 minutes. After washing them with PBS, DAB solution (SIGMA) were added thereto, and reaction was continued until color of the virus-infected focus are changed to reddish-brown. Then, after washing them with tap water and air-drying the same, number of virus-infected focus were counted.

Figure 19:
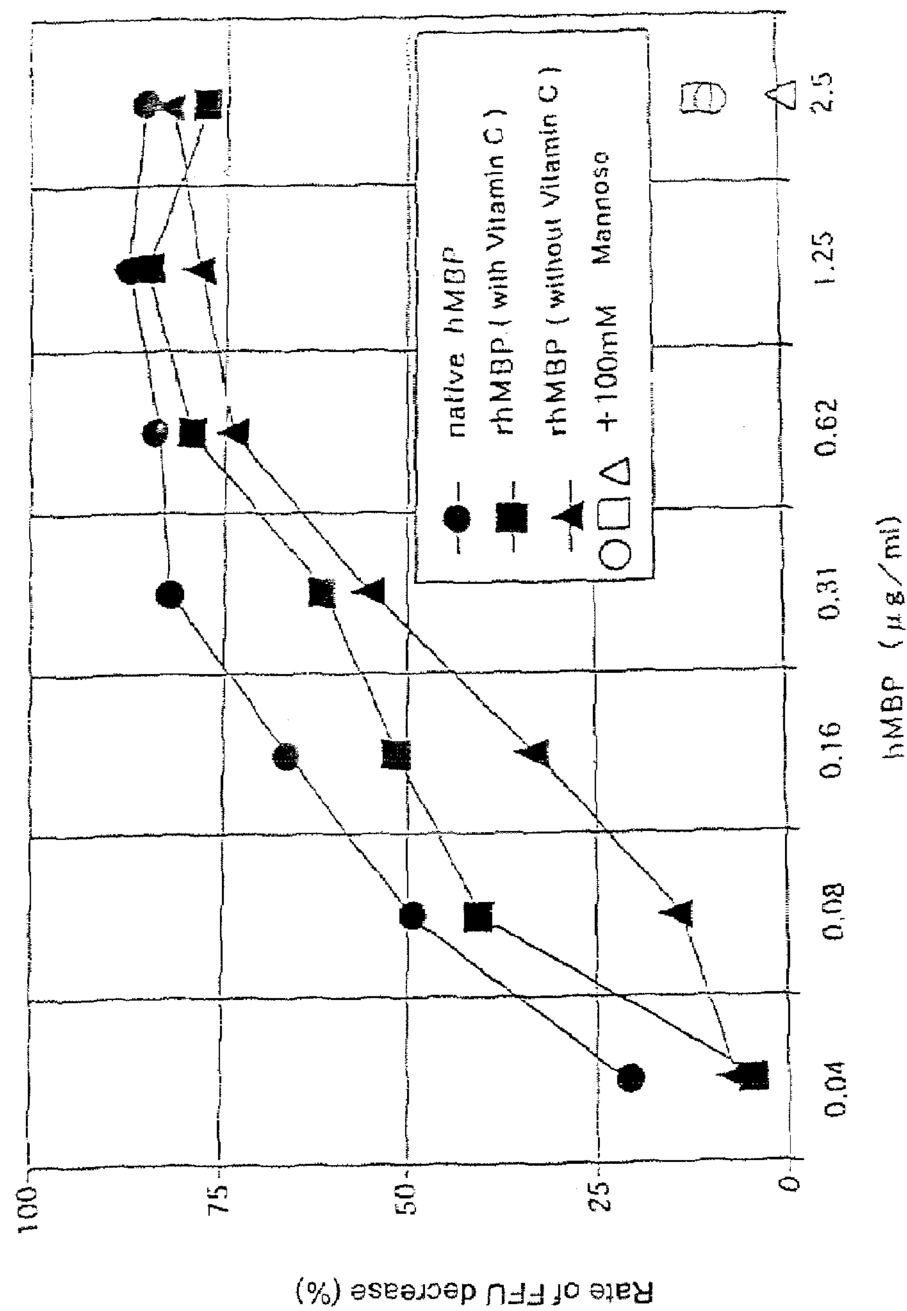
FIG. 19 is a graph showing activities by rhMBP to neutralize an infection of Influenza A virus.

FIG. 19 shows results obtained by comparison on the neutralization activities for influenza A viruses in the native hMBP, rhMBP fraction (cultured in the medium containing vitamin C), rhMBP fraction (cultivated in the medium without vitamin C) and said fractions combined these with 100 mM mannose. Neutralization titer were indicated as reduction rate of FFU based on 100% counts obtained, instead of MBP, from mixture of viral solution and TBSC only. As a result thereof, similar to the native hMBP, rhMBP (cultured with or without vitamin C) had neutralization activities for influenza virus, and such activities were inhibited by addition of mannose.

(3) Binding Activities to HIV-1, HBV and Influenza A virus

Binding activities on rhMBP to HIV-1, HBV and Influenza A virus were determined by electrophoresing the following viral structural proteins, transferring them to membranes, binding thereto rhMBP and detecting them with labeled antibody.

Necessary amounts of viral structural proteins for the electrophoresis were 0.25 μg of HIV-gp120 ($HIV_{IIIB}$-gp120) (ADVANCED BIOTECHNOLOGIES INCORPORATED (ABI)), 0.25 μg of HIV-gp160 ($HIV_{IIIB}$-gp160) (ABI), 10 μg of HBS (Hepatitis B Surface Antigen (HBsAg) (ABI), Subtype ad), Influenza A virus (IAV; presented by The Research Foundation For Osaka University Research Institute for Microbial Diseases), 5 μg of H1N1 Yamagata virion and 5 μg of $H_3N_2$ Beijin virion.

SDS-PAGE employed polyacrylamide gel having the concentration gradient of 4~20%, and HIV-1 and HBS were electrophoresed under reducing condition. After the electrophoresis, they were transferred to Immobilon-$P^{SQ}$ transfer membrane (Millipore) with NOVA BLOT™ electrophoretic transfer unit (Pharmacia) by using semi-dry electroblot buffer kit (Owl Scientific). After such transfer, they were blocked with BLOCKACE™ blocking solution (Dainippon Pharmaceutical) at room temperature for one hour. Then they were washed three times for 10 minutes with TBSTC (0.05% TWEEN 20 (Registered Trade Mark), 5 mM $CaCl_2$, TBS) or TBSTE (0.05% TWEEN 20 (Registered Trade Mark), 5 mM EDTA, TBS) (control which inhibits calcium ion ($Ca^{2+}$) dependent binding to carbohydrate recognition domain of rhMBP), and the solution diluted rhMBP to 1.0 μg/ml with TBSTC or TBSTE were reacted at room temperature for one hour.

In accordance with said procedure, after washing them with TBSTC or TBSTE, anti-human MBP polyclonal antibody diluted 1000 times with TBSTC were added thereto, and they were reacted at room temperature for one hour. After washing them with TBSTC, anti-rabbit IgG alkaline phosphatase label (Chemicon International) diluted 5000 times with TBSTC were added thereto, and they were reacted at room temperature for 30 minutes. After washing them with TBSTC, color were developed with NBT/BCIP (GIBCO).

Figure 20:
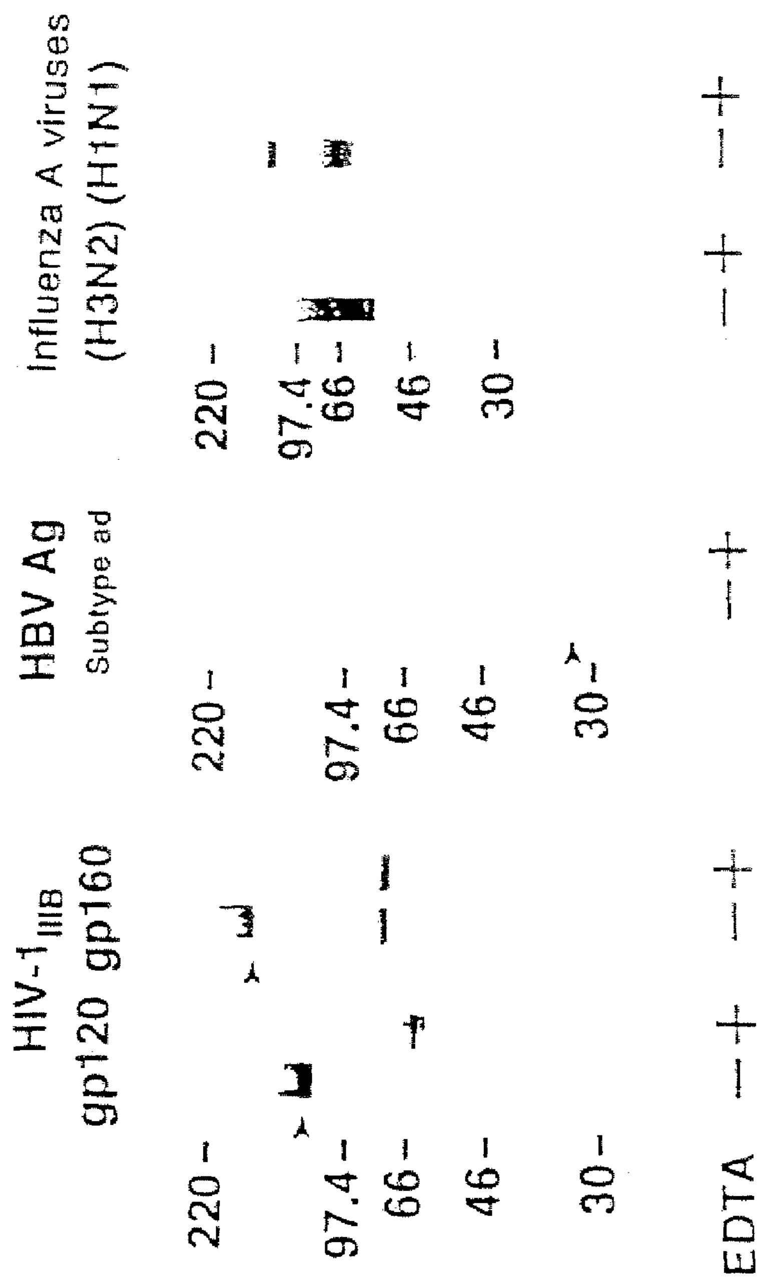
FIG. 20 is a graph showing activities by rhMBP to bind it to HIV-1, HBV and Influenza A virus.

Results are shown in FIG. 20. As shown in FIG. 20, it was demonstrated that the present rhMBP have binding activities to any of HIV-1, HBV and Influenza A virus.

EXAMPLE 8

Viral Growth (Infection Spread) Inhibition Activities (1) Viruses

Influenza A virus A/Ibaraki/1/90 employed in Example 6 were used.

(2) Viral Growth (Infection Spread) Inhibition Activities

MDCK cells were monolayer cultured in Eagle MEM medium containing 10% bovine fetal serum (GIBCO) on 24-well microtiter plates and influenza viruses were inoculated thereinto to be 30 FFU per well. After incubating them at 35' for 60 minutes, cells were washed and were added thereto 1 ml/well growth medium for influenza viruses containing 0.5% tragacanth gum. Further, native hMBP, rhMBP (cultured with vitamin C), rhMBP (cultured without vitamin C), bovine serum albumin were added thereto to be 0.5 μg/ml and 1 μg/ml per well, and they were cultured for three days.

Figure 21:
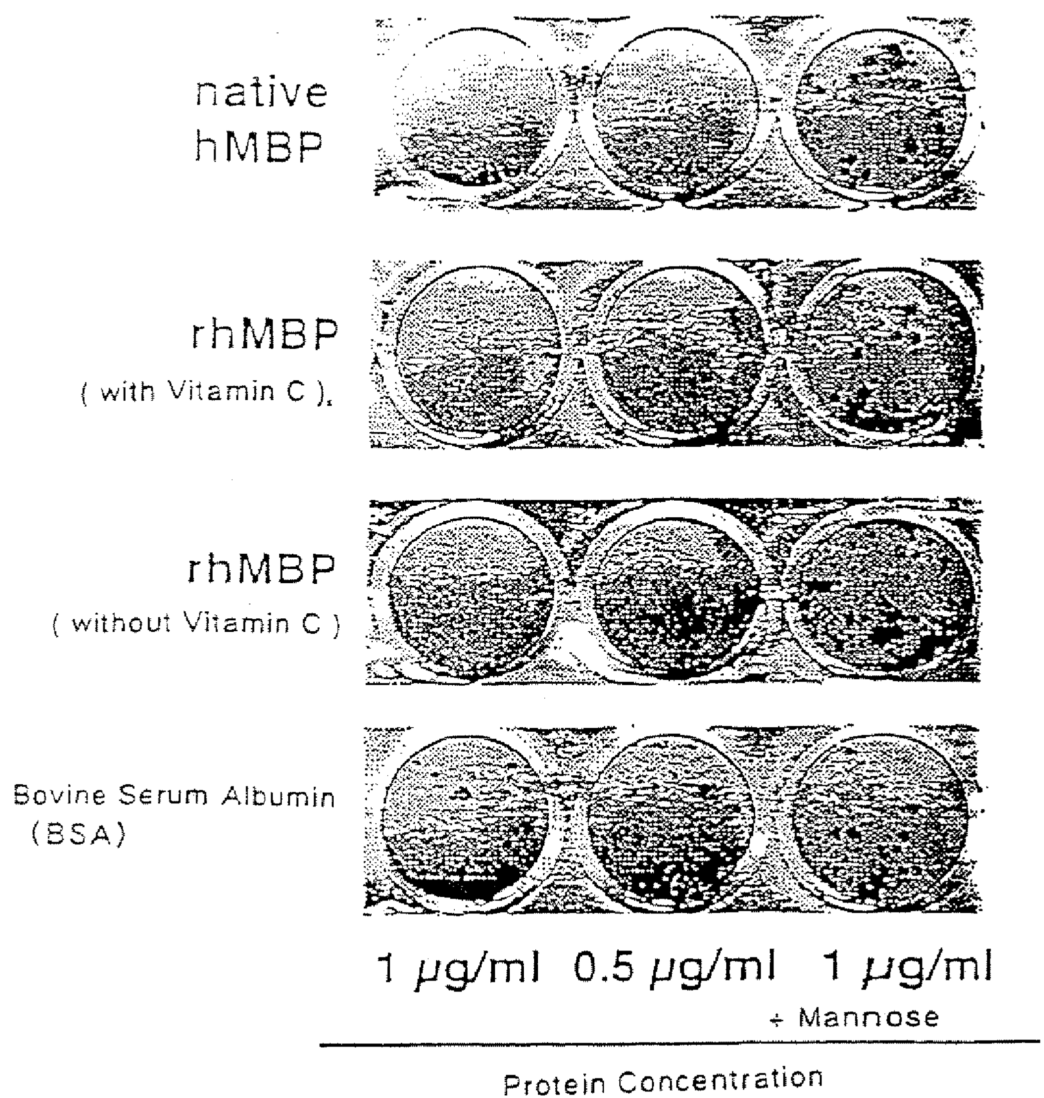
FIG. 21 shows activities by rhMBP to inhibit viral growth (infection spread).

After washing the cells, similar steps were taken along with Neutralization Activities of Example 7 (2), gross area of the virus-infected focus were determined with PAP staining. Results thereof are shown in FIG. 21. As a control, samples cultured under the co-presence of 100 mM mannose were employed (Right Column in FIG. 21). Apparently from the results shown in FIG. 21, rhMBP reduced focus area infected by influenza viruses concentration-dependently and exhibited an inhibition effect on viral growth.

EXAMPLE 9

Activities on rhMBP for Activating Complement (1) Viruses

As influenza A virus, A/lbaraki/l/90 (H3N2) employed in Example 6 were used.

(2) Preparation of Sensitized Sheep Erythrocyte

After washing Sheep Erythrocyte (Japan Biotest Institute) with gelatin-veronal buffer (1×veronal (145 mM NaCl, 15.6 mM 5,5-diethyl barbituric acid, 9.09 mM 5,5-diethyl sodium barbiturate), 1% gelatin, 0.25 mM $CaCl_2$, 0.82 mM $MgCl_2$), they were diluted with gelatin-veronal buffer to be its concentration of $1\times10^9$ cell/ml. After mixing them with 10 ml of Sheep Erythrocytet (1×10' cell/ml), 5 ml of chromium chloride (0.5 mg/ml) and 5 ml of mannan (60 μg/ml), then were incubated at room temperature for five minutes, and sensitized sheep erythrocyte were prepared by washing them several times with gelatin-veronal buffer and suspending the same into gelatin-veronal buffer to be readjusted its concentration of $1\times10^9$ cell/ml.

(3) Activation of Complement 400 μl of each of native hMBP and rhMBP (cultured with or without vitamin C) and 100 μl of sensitized sheep erythrocyte were mixed thereamong, the mixture so produced were incubated at room temperature for 15 minutes (each lectin concentration were 1, 10, 100 and 1000 ng/tube as a final concentration).

After the centrifugation, deposits were suspended in 1.1 ml of veronal buffer. 400 μl of guinea pig complement (ICN Pharmaceuticals: immanent MBP of which were removed with mannan-column and diluted 20 times with gelatin-veronal buffer) were added thereto, and they were incubated at 37° C. for 60 minutes and absorbance on supernatant were measured at 541 nm. Control was completely hemolyzed erythrocyte prepared by adding 1400 μl of distilled water to 100 μl of sensitized sheep erythrocyte. In an experiment on inhibition by mannose, sensitized sheep erythrocyte and hMBP were simultaneously added at the reaction.

Figure 22:
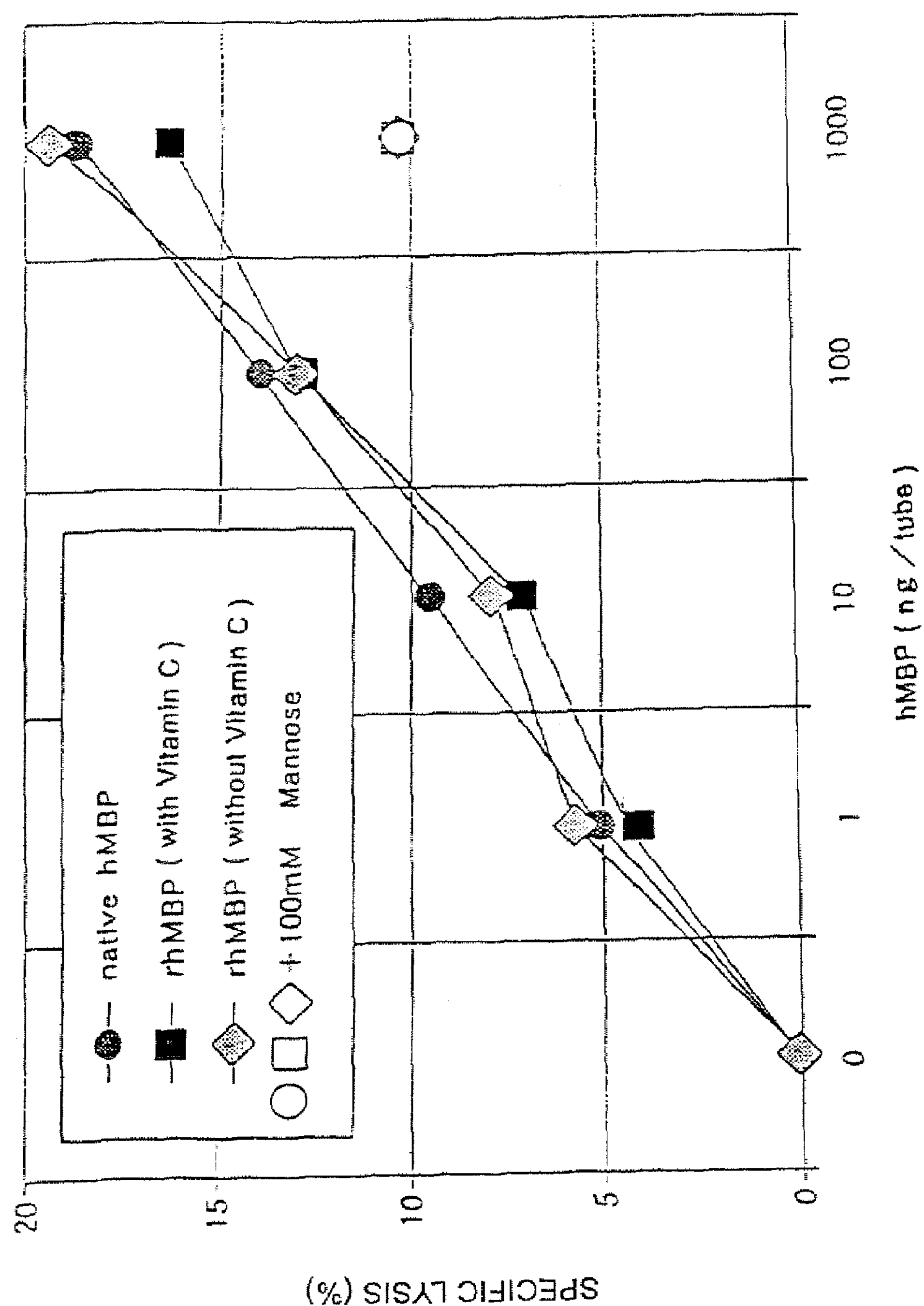
FIG. 22 is a graph showing solubility of Sheep Erythrocyte sensitized with rhMBP

Results thereof are shown in FIG. 22. As shown in FIG. 22, rhMBP (cultured with or without vitamin C) hemolyzed concentration-dependently sensitized sheep erythrocyte substantially like the native hMBP.

In view of this fact, it is deduced that rhMBP binds to mannan at the surface of the sensitized sheep erythrocyte, then the complements are activated accordingly. These activities were suppressed by an addition of mannose.

INDUSTRIAL APPLICABILITY

Accordingly, the present invention realizes means for the large-scale production of homogenous rhMBP which exhibits equivalent physiological activities to be offered by MBP obtained conventionally from living body with low yield. Since the present rhMBP have similar physiological activities to be offered by the native hMBP, they will offer the various effects including an application thereof to the medicine field.

The invention claimed is:

1. Recombinant Human Mannan-Binding Protein (rhMBP) produced by a Chinese Hamster Ovary (CHO) cell which:

lacks dihydrofolate reductase, possesses resistance to both neomycin and methotrexate, and is transformed with expression vector pNOW1-hMBP comprising the plasmid pNOW1 and cDNA consisting of the nucleotide sequence of SEQ ID NO. 2;

wherein the cDNA encodes the rhMBP, and wherein said cDNA is the continuous nucleotide sequence of from $66^{th}$ nucleotide to $812^{th}$ nucleotide in the nucleotide sequence of SEQ ID NO: 1.

2. The rhMBP according to claim 1 which has a specific peak at molecular weight of 1,000 kDa-1,300 kDa as determined by 280 nm absorbance in gel-filtration chromatography.

3. The rhMBP according to claim 1 which has a specific peak at molecular weights of 200 kDa -400 kDa as determined by 280 nm absorbance in gel-filtration chromatography.

4. The rhMBP according to claim 1 which has specific peaks at molecular weight of 1,000 kDa-1,300 kDa and 200 kDa-400 kDa as determined by 280 nm absorbance in gel-filtration chromatography.

* * * * *

UNITED STATES PATENT AND TRADEMARK OFFICE

CERTIFICATE OF CORRECTION

PATENT NO. : 7,572,890 B2
APPLICATION NO. : 11/241035
DATED : August 11, 2009
INVENTOR(S) : Nobutaka Wakamiya It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 681 days.

Signed and Sealed this

Seventh Day of September, 2010

David J. Kappos

*Director of the United States Patent and Trademark Office*

SEQUENCE LISTING

```
<160> NUMBER OF SEQ ID NOS: 28

<210> SEQ ID NO 1
<211> LENGTH: 3605
<212> TYPE: DNA
<213> ORGANISM: Homo sapiens
<220> FEATURE:
<221> NAME/KEY: CDS
<222> LOCATION: (66)..(809)
<220> FEATURE:
<221> NAME/KEY: mat_peptide
<222> LOCATION: (126)..(809)

<400> SEQUENCE: 1

ggtaaatatg tgttcattaa ctgagattaa ccttccctga gttttctcac accaaggtga      60

ggacc atg tcc ctg ttt cca tca ctc cct ctc ctt ctc ctg agt atg gtg     110
      Met Ser Leu Phe Pro Ser Leu Pro Leu Leu Leu Leu Ser Met Val
      -20                 -15                 -10

gca gcg tct tac tca gaa act gtg acc tgt gag gat gcc caa aag acc      158
Ala Ala Ser Tyr Ser Glu Thr Val Thr Cys Glu Asp Ala Gln Lys Thr
 -5              -1   1               5                  10

tgc cct gca gtg att gcc tgt agc tct cca ggc atc aac ggc ttc cca      206
Cys Pro Ala Val Ile Ala Cys Ser Ser Pro Gly Ile Asn Gly Phe Pro
            15                  20                  25

ggc aaa gat ggg cgt gat ggc acc aag gga gaa aag ggg gaa cca ggc      254
Gly Lys Asp Gly Arg Asp Gly Thr Lys Gly Glu Lys Gly Glu Pro Gly
        30                  35                  40

caa ggg ctc aga ggc tta cag ggc ccc cct gga aag ttg ggg cct cca      302
Gln Gly Leu Arg Gly Leu Gln Gly Pro Pro Gly Lys Leu Gly Pro Pro
    45                  50                  55

gga aat cca ggg cct tct ggg tca cca gga cca aag ggc caa aaa gga      350
Gly Asn Pro Gly Pro Ser Gly Ser Pro Gly Pro Lys Gly Gln Lys Gly
 60                  65                  70                  75

gac cct gga aaa agt ccg gat ggt gat agt agc ctg gct gcc tca gaa      398
Asp Pro Gly Lys Ser Pro Asp Gly Asp Ser Ser Leu Ala Ala Ser Glu
                80                  85                  90
```

-continued

```
aga aaa gct ctg caa aca gaa atg gca cgt atc aaa aag tgg ctg acc      446
Arg Lys Ala Leu Gln Thr Glu Met Ala Arg Ile Lys Lys Trp Leu Thr
            95                  100                 105

ttc tct ctg ggc aaa caa gtt ggg aac aag ttc ttc ctg acc aat ggt      494
Phe Ser Leu Gly Lys Gln Val Gly Asn Lys Phe Phe Leu Thr Asn Gly
        110                 115                 120

gaa ata atg acc ttt gaa aaa gtg aag gcc ttg tgt gtc aag ttc cag      542
Glu Ile Met Thr Phe Glu Lys Val Lys Ala Leu Cys Val Lys Phe Gln
    125                 130                 135

gcc tct gtg gcc acc ccc agg aat gct gca gag aat gga gcc att cag      590
Ala Ser Val Ala Thr Pro Arg Asn Ala Ala Glu Asn Gly Ala Ile Gln
140                 145                 150                 155

aat ctc atc aag gag gaa gcc ttc ctg ggc atc act gat gag aag aca      638
Asn Leu Ile Lys Glu Glu Ala Phe Leu Gly Ile Thr Asp Glu Lys Thr
                160                 165                 170

gaa ggg cag ttt gtg gat ctg aca gga aat aga ctg acc tac aca aac      686
Glu Gly Gln Phe Val Asp Leu Thr Gly Asn Arg Leu Thr Tyr Thr Asn
            175                 180                 185

tgg aac gag ggt gaa ccc aac aat gct ggt tct gat gaa gat tgt gta      734
Trp Asn Glu Gly Glu Pro Asn Asn Ala Gly Ser Asp Glu Asp Cys Val
        190                 195                 200

ttg cta ctg aaa aat ggc cag tgg aat gac gtc ccc tgc tcc acc tcc      782
Leu Leu Leu Lys Asn Gly Gln Trp Asn Asp Val Pro Cys Ser Thr Ser
    205                 210                 215

cat ctg gcc gtc tgt gag ttc cct atc tgaagggtca tatcactcag            829
His Leu Ala Val Cys Glu Phe Pro Ile
220                 225

gccctccttg tctttttact gcaacccaca ggcccacagt atgcttgaaa agataaatta    889

tatcaatttc ctcatatcca gtattgttcc ttttgtgggc aatcactaaa aatgatcact    949

aacagcacca acaaagcaat aatagtagta gtagtagtta gcagcagcag tagtagtcat   1009

gctaattata taatattttt aatatatact atgaggccct atcttttgca tcctacatta   1069

attatctagt ttaattaatc tgtaatgctt tcgatagtgt taacttgctg cagtatgaaa   1129

ataagacgga tttatttttc catttacaac aaacacctgt gctctgttga gccttccttt   1189

ctgtttgggt agagggctcc cctaatgaca tcaccacagt ttaataccac agctttttac   1249

caagtttcag gtattaagaa aatctatttt gtaactttct ctatgaactc tgtttttcttt  1309

ctaatgagat attaaaccat gtaaagaaca taaataacaa atctcaagca aacagcttca   1369

caaattctca cacacataca tacctatata ctcactttct agattaagat atgggacatt   1429

tttgactccc tagaagcccc gttataactc ctcctagtac taactcctag gaaaatacta   1489

ttctgacctc catgactgca cagtaatttc gtctgtttat aaacattgta tagttggaat   1549

catattgtgt gtaatgttgt atgtcttgct tactcagaat taagtctgtg agattcattc   1609

atgtcatgtg tacaaaagtt tcatcctttt cattgccatg tagggttccc ttatattaat   1669

attcctcagt tcatccattc tattgttaat aggcacttaa gtggcttcca atttttggcc   1729

atgaggaaga gaacccacga acattcctgg acttgtcttt tggtggacat ggtgcactaa   1789

tttcactacc tatccaggag tggaactggt agaggatgag gaaagcatgt attcagcttt   1849

agtagatatt accagttttc ctaagtgatt gtatgaattt atgctcctac cggcaatgtg   1909

tggcagtcct agatgctcta tgtgcttgta aaaagtcaat gttttcagtt ctcttgattt   1969

tcattattcc tgtggatgta aagtgatatt tccccatggt tttaatctgt atttccccaa   2029

catgtaataa ggttgaacac tttttttatat gcttattggg cacttgggta tcttcttctg  2089
```

-continued

```
tgaagtaccc gttcacattt ttgtattttg tttaaattag ttagccaata tttttcttac   2149

tgatttttaa gttattttta cattctgaat atgtcctttt taatgtgtat tacaaatatt   2209

ttgctagttt ttgacttgct cctaatgttg aattttgatg aacaaaattt cctaattttg   2269

agaaagtctt atttattcat attttctttc aaaattagtg ctttttgtgt catgtttaag   2329

aaatttttgc ccatcccaaa atcataagat atttttcatg attttgaaac catgaagaga   2389

tttttcatga ttttgaaatc atgaagatat ttttccattt ttttctaata gttttattaa   2449

taaacattct atctattcct ggtagaatag atatccactt gagacagcac tatgtaggaa   2509

agaccatttt tcctccactg aactagggtg gtgcattttt gtaagttagg taactgtatg   2569

tgtgtgtgtc tgtttctggg ctgtctattc tagtctattt gttgatgctt gtgtcaaaca   2629

gtacactatc ttaattattg tacatttata gttgtaactg tagtccagct ttgttcttct   2689

tcaagtcaag atttccatat aaatattaga aacagtttct caatttctac aaaatcctga   2749

tgaggtttct actgggacca cattgagtct atcaatcaac ttatgcagaa ctggcaactt   2809

actactgaat ctctaatcaa tgttcatcat gtatcgcttc atttaactag gatttctcta   2869

acttaattgc tatgttttga gatttttagt ttaaaaacct tgtatatctt gttttggtgg   2929

ttttagtgat tttaataata tattttaaat attttttctt ttctattgtt gtacacagaa   2989

atacagttaa gttttgtgtg tagtcttacg atgtttagta acctcaataa gtttatttct   3049

taaatctagt aatttgtaga ttcctctgga ttttgtatat gcatagtcat gtaagctgaa   3109

aatatggcaa tacttgcttc ttcccaattg ctttaccttt tttcttacct tattgcactg   3169

gttagcaacc ccaatacaga gaccaccaga gcaggtatag actcctgaaa gacaatataa   3229

tgaagtgctc cagtcaggcc tatctaaact ggattcacag ctctgtcact taattgctac   3289

atgatctaga gccagttact ttgtgtttca gccatgtatt tgcagctgag agaaaataat   3349

cattcttatt tcatgaaaat tgtggggatg atgaaataag ttaacacctt taaagtgtgt   3409

agtaaagtat caggatacta tattttaggt cttaatacac acagttatgc cgctagatac   3469

atgcttttta atgagataat gtgatattat acataacaca tatcgatttt taaaaattaa   3529

atcaaccttg ctttgatgga ataaactcca tttagtcaca aaaaaaaaaa aaaaaaaaaa   3589

aaaaaaaaaa aaaaaa                                                   3605
```

```
<210> SEQ ID NO 2
<211> LENGTH: 747
<212> TYPE: DNA
<213> ORGANISM: Homo sapiens

<400> SEQUENCE: 2

atgtccctgt ttccatcact ccctctcctt ctcctgagta tggtggcagc gtcttactca     60

gaaactgtga cctgtgagga tgcccaaaag acctgccctg cagtgattgc ctgtagctct    120

ccaggcatca acggcttccc aggcaaagat gggcgtgatg gcaccaaggg agaaaagggg    180

gaaccaggcc aagggctcag aggcttacag ggcccccctg gaaagttggg gcctccagga    240

aatccagggc cttctgggtc accaggacca aagggccaaa aaggagaccc tggaaaaagt    300

ccggatggtg atagtagcct ggctgcctca gaaagaaaag ctctgcaaac agaaatggca    360

cgtatcaaaa agtggctgac cttctctctg ggcaaacaag ttgggaacaa gttcttcctg    420

accaatggtg aaataatgac ctttgaaaaa gtgaaggcct tgtgtgtcaa gttccaggcc    480

tctgtggcca cccccaggaa tgctgcagag aatggagcca ttcagaatct catcaaggag    540

gaagccttcc tgggcatcac tgatgagaag acagaagggc agtttgtgga tctgacagga    600
```

```
aatagactga cctacacaaa ctggaacgag ggtgaaccca acaatgctgg ttctgatgaa    660

gattgtgtat tgctactgaa aaatggccag tggaatgacg tcccctgctc cacctcccat    720

ctggccgtct gtgagttccc tatctga                                        747


<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: sense DNA

<400> SEQUENCE: 3

tatgccgcgg aatcgatgat taccgtacgg aattcgggcc c                        41


<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: antisense
      DNA

<400> SEQUENCE: 4

acggcgcctt agctactaat ggcatgcctt aagcccggg                           39


<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: sense DNA

<400> SEQUENCE: 5

agcttccgcg gctgcaggga tccatcgat                                      29


<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: antisense
      DNA

<400> SEQUENCE: 6

aggcgccgac gtccctaggt agctattaa                                      29


<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: 5' sense
      primer (PS1)

<400> SEQUENCE: 7

ccccgcggga attctgtgga atgtgtgtca gttaggg                             37


<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:
      3' antisense primer (PS2)
```

```
<400> SEQUENCE: 8

ccctgcagct ttttgcaaaa gcctaggcct cc                                32


<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: 5' sense
      primer (PS3)

<400> SEQUENCE: 9

ccccgcggtg tggaatgtgt gtcagttagg g                                 31


<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: sense DNA

<400> SEQUENCE: 10

aattgggccc atcgat                                                  16


<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: antisense
      DNA

<400> SEQUENCE: 11

cccgggtagc tattaa                                                  16


<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: 5' sense
      primer (PD1)

<400> SEQUENCE: 12

ggctgcagtc cctcatgctt cgaccattga actgcatcgt c                      41


<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:
      3' antisense primer (PD2)

<400> SEQUENCE: 13

atagatctaa agccagcaaa agtcccatgg tc                                32


<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:  5' sense
      primer (PN1)

<400> SEQUENCE: 14
```

-continued

```
ggctgcagct tcacgctgcc gcaagcac                                    28


<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      3' antisense primer (PN2)

<400> SEQUENCE: 15

ggggatccgg ggtgggcgaa gaactccag                                   29


<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: antisense
      primer

<400> SEQUENCE: 16

atcttgttca agcatgcgaa acgatcct                                    28


<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: sense DNA

<400> SEQUENCE: 17

agcttgatat catcgatgcg gccgcggtac cagatctcgt acgtctagag            50


<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence:  antisense
      primer

<400> SEQUENCE: 18

actatagtag ctacgccggc gccatggtct agagcatgca gatctcttaa            50


<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: 5' sense
      primer (PC1)

<400> SEQUENCE: 19

ccgattactt accgccatgt tgacattgat tattgactag ttattaa               47


<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence:
      3' antisense primer (PC2)

<400> SEQUENCE: 20

ccatcgatcg gttcactaaa cgagctctgc ttatatagac ctccc                 45
```

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: 5' sense primer (PB11)

<400> SEQUENCE: 21
cctctagact gtgccttcta gttgccagcc at 32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: 3' antisense primer (PB12)

<400> SEQUENCE: 22
ccagatctgt acccatagag cccaccgcat cc 32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: 5' sense primer (PB21)

<400> SEQUENCE: 23
ttggatccct gtgccttcta gttgccagcc at 32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: 3' antisense primer (PB22)

<400> SEQUENCE: 24
ttcgtacgga tcccatagag cccaccgcat cc 32

<210> SEQ ID NO 25
<211> LENGTH: 7635
<212> TYPE: DNA
<213> ORGANISM: Artificial Sequence
<220> FEATURE:
<223> OTHER INFORMATION: Description of Artificial Sequence: plasmid pNOW1

<400> SEQUENCE: 25
gcgcgtttcg gtgatgacgg tgaaaacctc tgacacatgc agctcccgga gacggtcaca 60
gcttgtctgt aagcggatgc cgggagcaga caagcccgtc agggcgcgtc agcgggtgtt 120
ggcgggtgtc ggggctggct taactatgcg gcatcagagc agattgtact gagagtgcac 180
catatgccgc ggtgtggaat gtgtgtcagt tagggtgtgg aaagtcccca ggctccccag 240
caggcagaag tatgcaaagc atgcatctca attagtcagc aaccatagtc ccgcccctaa 300
ctccgcccat cccgccccta actccgccca gttccgccca ttctccgccc catggctgac 360
taattttttt tatttatgca gaggccgagg cgcctctgag ctattccaga agtagtgagg 420
aggctttttt ggaggcctag gcttttgcaa aaaagctgca gtgggcttac atggcgatag 480

-continued

```
ctagactggg cggttttatg gacagcaagc gaaccggaat tgccagctgg ggcgccctct   540

ggtaaggttg ggaagccctg caaagtaaac tggatggctt tcttgccgcc aaggatctga   600

tggcgcaggg gatcaagatc tgatcaagag acaggatgag gatcgtttcg catgattgaa   660

caagatggat tgcacgcagg ttctccggcc gcttgggtgg agaggctatt cggctatgac   720

tgggcacaac agacaatcgg ctgctctgat gccgccgtgt tccggctgtc agcgcagggg   780

cgcccggttc tttttgtcaa gaccgacctg tccggtgccc tgaatgaact gcaggacgag   840

gcagcgcggc tatcgtggct ggccacgacg ggcgttcctt gcgcagctgt gctcgacgtt   900

gtcactgaag cgggaaggga ctggctgcta ttgggcgaag tgccggggca ggatctcctg   960

tcatctcacc ttgctcctgc cgagaaagta tccatcatgg ctgatgcaat gcggcggctg  1020

catacgcttg atccggctac ctgcccattc gaccaccaag cgaaacatcg catcgagcga  1080

gcacgtactc ggatggaagc cggtcttgtc gatcaggatg atctggacga agagcatcag  1140

gggctcgcgc cagccgaact gttcgccagg ctcaaggcgc gcatgcccga cggcgaggat  1200

ctcgtcgtga cccatggcga tgcctgcttg ccgaatatca tggtggaaaa tggccgcttt  1260

tctggattca tcgactgtgg ccggctgggt gtggcggacc gctatcagga catagcgttg  1320

gctacccgtg atattgctga agagcttggc ggcgaatggg ctgaccgctt cctcgtgctt  1380

tacggtatcg ccgctcccga ttcgcagcgc atcgccttct atcgccttct tgacgagttc  1440

ttctgagcgg gactctgggg ttcgaaatga ccgaccaagc gacgcccaac ctgccatcac  1500

gagatttcga ttccaccgcc gccttctatg aaaggttggg cttcggaatc gttttccggg  1560

acgccggctg gatgatcctc cagcgcggga tcacatgctg gattcttcgc ccacccccctc  1620

gatcccctcg cgagttggtt cagctgctgc ctgaggctgg acgacctcgc ggagttctac  1680

cggcagtgca aatccgtcgg catccaggaa accagcagcg gctatccgcg catccatgcc  1740

cccgaactgc aggagtgggg aggcacgatg gccgctttgg tcgacccgga cgggacgctc  1800

ctgcgcctga tacagaacga attgcttgca ggcatctcat gagtgtgtct tcccgttttc  1860

cgcctgaggt cactgcgtgg atgggatccg tgacataatt ggacaaacta cctacagaga  1920

tttaaagctc taaggtaaat ataaaatttt taagtgtata atgtgttaaa ctactgattc  1980

taattgtttg tgtattttag attccaacct atggaactga tgaatgggag cagtggtgga  2040

atgcctttaa tgaggaaaac ctgttttgct cagaagaaat gccatctagt gatgatgagg  2100

ctactgctga ctctcaacat tctactcctc caaaaaagaa gagaaaggta gaagacccca  2160

aggactttcc ttcagaattg ctaagttttt tgagtcatgc tgtgtttagt aatagaactc  2220

ttgcttgctt tgctatttac accacaaagg aaaaagctgc actgctatac cagaaattat  2280

gaaatattct gtaaccttta taagtaggca taacagttat aatcataaca tactgttttt  2340

tcttactcca cacaggcata gagtgtctgc tattaataac tatgctcaaa aattgtgtac  2400

ctttagcttt ttaatttgta aaggggttaa taaggaatat ttgatgtata gtgccttgac  2460

tagagatcat aatcagccat accacatttg tagaggtttt acttgcttta aaaaacctcc  2520

cacacctccc cctgaacctg aaacataaaa tgaatgcaat tgttgttgtt aacttgttta  2580

ttgcagctta taatggttac aaataaagca atagcatcac aaatttcaca aataaagcat  2640

ttttttcact gcattctagt tgtggtttgt ccaaactcat caatgtatct tatcatgtct  2700

gggcccgata tccgatgtac gggccagata tacgcgttga cattgattat tgactagtta  2760

ttaatagtaa tcaattacgg ggtcattagt tcatagccca tatatggagt tccgcgttac  2820

ataacttacg gtaaatggcc cgcctggctg accgcccaac gacccccgcc cattgacgtc  2880
```

-continued

```
aataatgacg tatgttccca tagtaacgcc aatagggact ttccattgac gtcaatgggt   2940
ggactattta cggtaaactg cccacttggc agtacatcaa gtgtatcata tgccaagtac   3000
gccccctatt gacgtcaatg acggtaaatg gcccgcctgg cattatgccc agtacatgac   3060
cttatgggaa ctttcctact tggcagtaca tctacgtatt agtcatcgct attaccatgg   3120
tgatgcggtt ttggcagtac atcaatgggc gtggatagcg gtttgactca cggggatttc   3180
caagtctcca ccccattgac gtcaatggga gtttgttttg gcaccaaaat caacgggact   3240
ttccaaaatg tcgtaacaac tccgccccat tgacgcaaat gggcggtagg cgtgtacggt   3300
gggaggtcta tataagcaga gcatcgatgc ggccgcggta cctctagact gtgccttcta   3360
gttgccagcc atctgttgtt tggccccccc tcccccgtgc cttccttgac cctggaaggt   3420
gccactccca ctgtcctttc ctaataaaat gaggaaattg catcgcattg tctgagtagg   3480
tgtcattcta ttctgggggg tggggtgggg caggacagca agggggagga ttgggaagac   3540
aatagcaggc atgctgggga tgcggtgggc tctatggtct aggctgtgcc ttctagttgc   3600
cagccatctg ttgtttggcc cccctccccc cgtgccttcc ttgaccctgg aaggtgccac   3660
tcccactgtc ctttcctaat aaaatgagga aattgcatcg cattgtctga gtaggtgtca   3720
ttctattctg gggggtgggg tggggcagga cagcaagggg gaggattggg aagacaatag   3780
caggcatgct ggggatgcgg tgggctctat ggcgtacggg atgctagaga attctgtgga   3840
atgtgtgtca gttagggtgt ggaaagtccc caggctcccc agcaggcaga agtatgcaaa   3900
gcatgcatct caattagtca gcaaccatag tcccgcccct aactccgccc atcccgcccc   3960
taactccgcc cagttccgcc cattctccgc cccatggctg actaattttt tttatttatg   4020
cagaggccga ggcgcctctg agctattcca gaagtagtga ggaggctttt ttggaggcct   4080
aggcttttgc aaaaaagctg cagtccctca tggttcgacc attgaactgc atcgtcgccg   4140
tgtcccaaaa tatggggatt ggcaagaacg gagacctacc ctggcctccg ctcaggaacg   4200
agttcaagta cttccaaaga atgaccacaa cctcttcagt ggaaggtaaa cagaatctgg   4260
tgattatggg taggaaaacc tggttctcca ttcctgagaa gaatcgacct ttaaaggaca   4320
gaattaatat agttctcagt agagaactca aagaaccacc acgaggagct cattttcttg   4380
ccaaaagttt ggatgatgcc ttaagactta ttgaacaacc ggaattgtca agtaaagtag   4440
acatggtttg gatagtcgga ggcagttctg tttaccagga agccatgaat caaccaggcc   4500
acctcagact ctttgtgaca aggatcatgc aggaatttga aagtgacacg tttttcccag   4560
aaattgattt ggggaaatat aaacttctcc cagaataccc aggcgtcctc tctgaggtcc   4620
aggaggaaaa aggcatcaag tataagtttg aagtctacga gaagaaagac taacaggaag   4680
atgctttcaa gttctctgct cccctcctaa agctatgcat ttttataaga ccatgggact   4740
tttgctggct ttaagatccg tgacataatt ggacaaacta cctacagaga tttaaagctc   4800
taaggtaaat ataaaatttt taagtgtata atgtgttaaa ctactgattc taattgtttg   4860
tgtattttag attccaacct atggaactga tgaatgggag cagtggtgga atgcctttaa   4920
tgaggaaaac ctgttttgct cagaagaaat gccatctagt gatgatgagg ctactgctga   4980
ctctcaacat tctactcctc caaaaaagaa gagaaaggta gaagacccca aggactttcc   5040
ttcagaattg ctaagttttt tgagtcatgc tgtgtttagt aatagaactc ttgcttgctt   5100
tgctatttac accacaaagg aaaaagctgc actgctatac cagaaattat gaaatattct   5160
gtaaccttta taagtaggca taacagttat aatcataaca tactgttttt tcttactcca   5220
```

-continued

```
cacaggcata gagtgtctgc tattaataac tatgctcaaa aattgtgtac ctttagcttt   5280
ttaatttgta aaggggttaa taaggaatat ttgatgtata gtgccttgac tagagatcat   5340
aatcagccat accacatttg tagaggtttt acttgcttta aaaaacctcc cacacctccc   5400
cctgaacctg aaacataaaa tgaatgcaat tgttgttgtt aacttgttta ttgcagctta   5460
taatggttac aaataaagca atagcatcac aaatttcaca aataaagcat ttttttcact   5520
gcattctagt tgtggtttgt ccaaactcat caatgtatct tatcatgtct gggcccctgc   5580
attaatgaat cggccaacgc gcggggagag gcggtttgcg tattgggcgc tcttccgctt   5640
cctcgctcac tgactcgctg cgctcggtcg ttcggctgcg gcgagcggta tcagctcact   5700
caaaggcggt aatacggtta tccacagaat caggggataa cgcaggaaag aacatgtgag   5760
caaaaggcca gcaaaaggcc aggaaccgta aaaaggccgc gttgctggcg tttttccata   5820
ggctccgccc ccctgacgag catcacaaaa atcgacgctc aagtcagagg tggcgaaacc   5880
cgacaggact ataaagatac caggcgtttc cccctggaag ctccctcgtg cgctctcctg   5940
ttccgaccct gccgcttacc ggatacctgt ccgcctttct cccttcggga agcgtggcgc   6000
tttctcaatg ctcacgctgt aggtatctca gttcggtgta ggtcgttcgc tccaagctgg   6060
gctgtgtgca cgaacccccc gttcagcccg accgctgcgc cttatccggt aactatcgtc   6120
ttgagtccaa cccggtaaga cacgacttat cgccactggc agcagccact ggtaacagga   6180
ttagcagagc gaggtatgta ggcggtgcta cagagttctt gaagtggtgg cctaactacg   6240
gctacactag aaggacagta tttggtatct gcgctctgct gaagccagtt accttcggaa   6300
aaagagttgg tagctcttga tccggcaaac aaaccaccgc tggtagcggt ggtttttttg   6360
tttgcaagca gcagattacg cgcagaaaaa aaggatctca agaagatcct ttgatctttt   6420
ctacggggtc tgacgctcag tggaacgaaa actcacgtta agggattttg gtcatgagat   6480
tatcaaaaag gatcttcacc tagatccttt taaattaaaa atgaagtttt aaatcaatct   6540
aaagtatata tgagtaaact tggtctgaca gttaccaatg cttaatcagt gaggcaccta   6600
tctcagcgat ctgtctattt cgttcatcca tagttgcctg actccccgtc gtgtagataa   6660
ctacgatacg ggagggctta ccatctggcc ccagtgctgc aatgataccg cgagacccac   6720
gctcaccggc tccagattta tcagcaataa accagccagc cggaagggcc gagcgcagaa   6780
gtggtcctgc aactttatcc gcctccatcc agtctattaa ttgttgccgg gaagctagag   6840
taagtagttc gccagttaat agtttgcgca acgttgttgc cattgctaca ggcatcgtgg   6900
tgtcacgctc gtcgtttggt atggcttcat tcagctccgg ttcccaacga tcaaggcgag   6960
ttacatgatc ccccatgttg tgcaaaaaag cggttagctc cttcggtcct ccgatcgttg   7020
tcagaagtaa gttggccgca gtgttatcac tcatggttat ggcagcactg cataattctc   7080
ttactgtcat gccatccgta agatgctttt ctgtgactgg tgagtactca accaagtcat   7140
tctgagaata gtgtatgcgg cgaccgagtt gctcttgccc ggcgtcaata cgggataata   7200
ccgcgccaca tagcagaact ttaaaagtgc tcatcattgg aaaacgttct tcggggcgaa   7260
aactctcaag gatcttaccg ctgttgagat ccagttcgat gtaacccact cgtgcaccca   7320
actgatcttc agcatctttt actttcacca gcgtttctgg gtgagcaaaa acaggaaggc   7380
aaaatgccgc aaaaaaggga ataagggcga cacggaaatg ttgaatactc atactcttcc   7440
tttttcaata ttattgaagc atttatcagg gttattgtct catgagcgga tacatatttg   7500
aatgtattta gaaaaataaa caaatagggg ttccgcgcac atttccccga aaagtgccac   7560
ctgacgtcta agaaaccatt attatcatga cattaaccta taaaaatagg cgtatcacga   7620
```

```
ggccctttcg tcctc                                                     7635


<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 26

aaggaaaaaa gcggccgcat gtccctgttt ccatcactc                            39


<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 27

gctctagatc agatagggaa ctcacagac                                      29


<210> SEQ ID NO 28
<211> LENGTH: 248
<212> TYPE: PRT
<213> ORGANISM: Homo sapiens

<400> SEQUENCE: 28

Met Ser Leu Phe Pro Ser Leu Pro Leu Leu Leu Leu Ser Met Val Ala
  1               5                  10                  15

Ala Ser Tyr Ser Glu Thr Val Thr Cys Glu Asp Ala Gln Lys Thr Cys
             20                  25                  30

Pro Ala Val Ile Ala Cys Ser Ser Pro Gly Ile Asn Gly Phe Pro Gly
         35                  40                  45

Lys Asp Gly Arg Asp Gly Thr Lys Gly Glu Lys Gly Glu Pro Gly Gln
     50                  55                  60

Gly Leu Arg Gly Leu Gln Gly Pro Pro Gly Lys Leu Gly Pro Pro Gly
 65                  70                  75                  80

Asn Pro Gly Pro Ser Gly Ser Pro Gly Pro Lys Gly Gln Lys Gly Asp
                 85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240
```

-continued

```
Leu Ala Val Cys Glu Phe Pro Ile
                245
```